United States Patent
Marks et al.

(10) Patent No.: US 12,422,431 B2
(45) Date of Patent: Sep. 23, 2025

(54) CAPTURE FLOW ASSAY DEVICE AND METHODS

(71) Applicant: B. G. NEGEV TECHNOLOGIES AND APPLICATIONS LTD., AT BEN-GURION UNIVERSITY, Beer Sheva (IL)

(72) Inventors: Robert Marks, Omer (IL); Tim Axelrod, Haniel (IL); Ariel Kushmaro, Beer Yaakov (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 1071 days.

(21) Appl. No.: 17/419,865

(22) PCT Filed: Dec. 31, 2019

(86) PCT No.: PCT/IL2019/051446
§ 371 (c)(1),
(2) Date: Jun. 30, 2021

(87) PCT Pub. No.: WO2020/141525
PCT Pub. Date: Jul. 9, 2020

(65) Prior Publication Data
US 2022/0082560 A1 Mar. 17, 2022

Related U.S. Application Data

(60) Provisional application No. 62/786,611, filed on Dec. 31, 2018.

(51) Int. Cl.
*G01N 33/543* (2006.01)
*B01L 3/00* (2006.01)

(52) U.S. Cl.
CPC ...... *G01N 33/54388* (2021.08); *B01L 3/5023* (2013.01); *B01L 2300/0645* (2013.01); *B01L 2300/0663* (2013.01); *B01L 2300/069* (2013.01)

(58) Field of Classification Search
CPC ..... G01N 33/54388; G01N 2021/8488; G01N 21/8483; B01L 3/5023; B01L 3/50273;
(Continued)

(56) References Cited

U.S. PATENT DOCUMENTS

2007/0172963 A1  7/2007  Krauth et al.
2007/0243630 A1  10/2007  Boehringer et al.
(Continued)

FOREIGN PATENT DOCUMENTS

CN  1879019 A  12/2006
CN  103293134 A  9/2013
(Continued)

OTHER PUBLICATIONS

Mayeux, R., "Biomarkers: potential uses and limitations", NeuroRx, Apr. 2004; 1(2): 182-188.
(Continued)

*Primary Examiner* — Kathryn Elizabeth Limbaugh
(74) *Attorney, Agent, or Firm* — The Roy Gross Law Firm, LLC; Roy D. Gross

(57) ABSTRACT

Disclosed is a device including at least a section 1, a section 2, a section 3 and a section 4 wherein section 2 is coupled to section 1, section 3 is coupled to section 2 and comprises a surface functionalized with an analyte or equivalent thereof, section 4 is coupled to section 3, and section 1, section 2, section 3 and section 4 are arranged along a horizontal axis and in fluid communication allowing lateral flow from section 1 throughout all sections to section 4.
(Continued)

Disclosed are also a kit and method for determining and quantifying the presence of an analyte in a sample.

20 Claims, 17 Drawing Sheets

(58) Field of Classification Search
CPC ..... B01L 2300/0645; B01L 2300/0663; B01L 2300/069; B01L 2300/0819; B01L 2300/0825; B01L 2300/126; B01L 2200/10; B01L 2400/0406
See application file for complete search history.

(56) References Cited

U.S. PATENT DOCUMENTS

| | | | |
|---|---|---|---|
| 2008/0014657 | A1 | 1/2008 | Lovell et al. |
| 2016/0274104 | A1* | 9/2016 | Aminoff ............... G06T 7/0012 |
| 2017/0059563 | A1* | 3/2017 | Smith ................ G01N 21/6454 |
| 2018/0306709 | A1* | 10/2018 | Zaccari ..................... G06T 7/90 |
| 2020/0132686 | A1 | 4/2020 | Chowers et al. |
| 2021/0003579 | A1 | 1/2021 | Honjo et al. |
| 2021/0405044 | A1 | 12/2021 | Yang et al. |
| 2022/0082560 | A1 | 3/2022 | Marks et al. |
| 2023/0258644 | A1 | 8/2023 | Marks et al. |

FOREIGN PATENT DOCUMENTS

| | | |
|---|---|---|
| DE | 202018102600 U1 | 6/2018 |
| EP | 3278108 A1 | 2/2018 |
| EP | 4257981 A1 | 10/2023 |
| WO | 2015168515 A1 | 11/2015 |
| WO | 2022153316 A1 | 7/2022 |

OTHER PUBLICATIONS

Grange, R. D., "Radioimmunoassay, enzyme and non-enzyme-based immunoassays", Br. J. Anaesth. 112, 213-216 (2014).
O'Farrell, B., "Lateral Flow Technology for Field-Based Applications—Basics and Advanced Developments", Top. Companion Anim. Med. 30, 139-147 (2015).
Posthuma-Trumpie, G. A., Korf, J. & Van Amerongen, A. "Lateral flow (immuno)assay: Its strengths, weaknesses, opportunities and threats. A literature survey", Anal. Bioanal. Chem. 393, 569-582 (2009).
Warren, A. D., Kwong, G. A., Wood, D. K., Lin, K. Y. & Bhatia, S. N. "Point-of-care diagnostics for noncommunicable diseases using synthetic urinary biomarkers and paper microfluidics", Proc. Natl. Acad. Sci. 111, 3671-3676 (2014).
Li, Z. et al. "Rapid and sensitive detection of protein biomarker using a portable fluorescence biosensor based on quantum dots and a lateral flow test strip", Anal. Chem. 82, 7008-14 (2010).
He, Y. et al. "Ultrasensitive nucleic acid biosensor based on enzyme-gold nanoparticle dual label and lateral flow strip biosensor", Biosens. Bioelectron. 26, 2018-2024 (2011).
Mao, X. et al. "Disposable Nucleic Acid Biosensors Based on Gold Nanoparticle Probes and Lateral Flow Strip" 8Anal. Chem. 2009, 81, 4, 1660-1668.
Verheijen, R., Osswald, I. K., Dietrich, R. & Haasnoot, W. "Development of a one step strip test for the detection of (dihydro)streptomycin residues in raw milk", Food Agric. Immunol. 12, 31-40 (2000).
Delmulle, B. S., De Saeger, S. M. D. G., Sibanda, L., Barna-Vetro, I. & Van Peteghem, C. H. "Development of an Immunoassay-based lateral flow dipstick for the rapid detection of aflatoxin B1in pig feed", J. Agric. Food Chem. 53, 3364-3368 (2005).
Guo, Y. R., Liu, S. Y., Gui, W. J. & Zhu, G. N. "Gold immunochromatographic assay for simultaneous detection of carbofuran and triazophos in water samples", Anal. Biochem. 389, 32-39 (2009).
Fisher, M. et al. "A combined immunomagnetic separation and lateral flow method for a sensitive on-site detection of Bacillus anthracis spores—Assessment in water and dairy products", Lett. Appl. Microbiol. 48, 413-418 (2009).
Byzova, N. A. et al. "Development of an immunochromatographic test system for the detection of human epidermal growth factor", Appl. Biochem. Microbiol. 49, 606-612 (2013).
Liu, G. et al. "Aptamer-nanoparticle strip biosensor for sensitive detection of cancer cells", Anal. Chem. 81, 10013-10018 (2009).
Huo, T., Peng, C., Xu, C. & Liu, L. "Immumochromatographic assay for determination of hexoestrol residues", Eur. Food Res. Technol. 225, 743-747 (2007).
Posthuma-Trumpie, G. A., Korf, J. & Van Amerongen, A. "Development of a competitive lateral flow immunoassay for progesterone: Influence of coating conjugates and buffer components", Anal. Bioanal. Chem. 392, 1215-1223 (2008).
Sajid, M., Kawde, A. N. & Daud, M. "Designs, formats and applications of lateral flow assay: A literature review", J. Saudi Chem. Soc. 19, 689-705 (2014).
Moghadam, B. Y., Connelly, K. T. & Posner, J. D. "Two orders of magnitude improvement in detection limit of lateral flow assays using isotachophoresis", Anal. Chem. 87, 1009-1017 (2015).
Kumar, S., Bhushan, P., Krishna, V. & Bhattacharya, S. "Tapered lateral flow immunoassay based point-of-care diagnostic device for ultrasensitive colorimetric detection of dengue NS1", Biomicrofluidics 12, 12(3): 034104. (2018).
Myers, Frank B., and Luke P. Lee. "Innovations in optical microfluidic technologies for pointof-care diagnostics." Lab Chip. Dec. 2008;8(12):2015-31.
PCT Search Report for International No. PCT/IL2019/051446; Completed Apr. 28, 2020; Mailed Apr. 28, 2020. 3 pages.
PCT Written Opinion for International No. PCT/IL2019/051446; Completed Apr. 28, 2020; Mailed Apr. 28, 2020. 5 pages.

* cited by examiner

CAPTURE FLOW ASSAY DEVICE AND METHODS

CROSS REFERENCE TO RELATED APPLICATIONS

This application is a National Phase of PCT Patent Application No. PCT/IL2019/051446 having International filing date of Dec. 31, 2019, entitled "CAPTURE FLOW ASSAY DEVICE AND METHODS", which claims the benefit of priority of U.S. Provisional Patent Application No. 62/786,611, filed Dec. 31, 2018, entitled "CAPTURE FLOW ASSAY DEVICE AND METHODS". The contents of the above applications are all incorporated by reference as if fully set forth herein in their entirety.

FIELD OF THE INVENTION

The present invention is in the field of binding assay methods and apparatus for testing biological samples.

BACKGROUND OF THE INVENTION

In the last years, there is a need to deliver care closer to the patient and therefore a need for the development of testing methods that can be performed outside of the conventional laboratory.

The tests that can be performed using point-of-care-testing (POCT) devices has expanded considerably. There is still a need for improvements so that devices are easier to use, less prone to errors, more compact or smaller. Moreover, there are areas where new technologies are needed in order to deliver the required analytical performance. Infectious disease is one such areas where existing technology is not sufficiently sensitive. Furthermore, quantitation technology is still missing in the POCT field.

SUMMARY OF THE INVENTION

The present invention, in some embodiments, relates to a lateral flow device. In some embodiments, the device is a point of care testing device.

According to an aspect of the present invention, there is provided a device, comprising a section 1, a section 2, a section 3 and a section 4, wherein the section 2 is coupled to the section 1; the section 3 is coupled to the section 2 and to the section 4, the section 3 comprises a surface functionalized with an analyte or equivalent thereof; sections 1 to 4 are arranged along a horizontal axis and in fluid communication allowing lateral flow of fluid from the section 1 through the section 2 and the section 3 to section 4.

In one embodiment, the section 1 comprises a sample collecting surface; the section 2 comprises a surface comprising a recognition molecule having specific affinity to the analyte, wherein the recognition molecule is linked to a reporter molecule, and wherein the reporter molecule generates a trigger; and the section 4 comprises a surface in contact with a substrate molecule generating a signal in response to the trigger.

In one embodiment, the device further comprises a calibration area disposed between section 2 and section 3, wherein the calibration area comprises a surface in contact with the substrate molecule.

In one embodiment, the device further comprises a section 5 coupled to the section 4 and in fluid communication with the section 4.

In one embodiment, coupled is in contact or partially overlapping.

In one embodiment, the trigger comprises at least one of: a reactive compound, electromagnetic radiation, and a charged particle or a combination thereof.

In one embodiment, the section 3 is devoid of the recognition molecule and the reporter molecule.

In one embodiment, the concentration of the recognition molecule in section 2 and the analyte in section 3 is in the range of 0.01 µg/mL to 100 mg/mL.

In one embodiment, the reporter molecule is selected from an enzyme, luminescent compound, fluorescent compound, magnetic particle, electrochemically active compound.

In one embodiment, at least three sections are disposed along one or more planes.

In one embodiment, two consecutive sections are disposed along one or more planes.

In one embodiment, all of the sections are disposed along the same plane.

In one embodiment, the overlapping is in the range of 0.01% to 99% of the total surface of the section.

In one embodiment, the device further comprises a detection unit in operable communication with the device, and wherein the detection unit is configured to detect the signal.

In one embodiment, the detection unit comprises an element selected form the group consisting of an active-pixel sensor (APS), an electrode, an excitation source with active-pixel sensor, or any combination thereof.

In one embodiment, the analyte or equivalent thereof is selected from virus, proteins, biological cells, toxins and pathogens, pharmaceuticals and drugs.

In one embodiment, the sample is selected from water, blood, urine, sweat, saliva, and serum.

According to another aspect of the invention, there is provided a method for determining the presence of an analyte in a sample, comprising: contacting a sample with a device of the invention; and detecting the presence of a signal, thereby determining the presence of the analyte in a sample.

In one embodiment, section 1 comprises a sample collecting surface; section 2 comprises a surface deposited with a recognition molecule having specific affinity to analyte linked to a reported molecule, wherein the reporter molecule generates a chemically and/or electrically and/or a physically detectable reaction; section 4 comprises a surface deposited with a substrate; and section 5 comprises a surface available for holding excess sample.

In one embodiment, the device further comprises a calibration area comprising a substrate placed between section 2 and section 3.

In one embodiment, the sample diffuses from section 1 to section 5.

In one embodiment, there is provided a method for quantifying the amount of an analyte in a sample, further comprising quantifying the amount of the signal in calibration area; and correlating the signal intensity data from calibration area with signal intensity data from section 4.

In one embodiment, there is provided a method for diagnosing an infectious disease.

According to another aspect of the present invention, there is provided a kit, comprising: a section 1, a section 2, a section 3, and a section 4; an analyte or equivalent thereof; a recognition molecule having specific affinity to the analyte linked to a reporter molecule, wherein the reporter molecule generates a chemically and/or electrically and/or a physically detectable reaction; and a substrate reacting in the presence of the reporter molecule.

In one embodiment, the kit further comprises instructions for depositing section 2 with the reporter molecule, section 3 with the analyte and section 4 with a substrate.

According to an aspect of the present invention, there is provided a kit, comprising: a section 1 comprising a sample collecting surface, section 2, comprising a surface deposited with a recognition molecule having specific affinity to the analyte linked to a reporter molecule, wherein the reporter molecule generates a chemically and/or electrically and/or a physically detectable reaction; a section 3 functionalized with the analyte; a section 4 comprising a surface deposited with a substrate; and a section 5 comprising a surface available for holding excess sample.

In one embodiment, the kit further comprises a calibration area.

In one embodiment, the kit further comprises instructions for arranging section 1, section 2, calibration area, section 3, section 4 and section 5 along a horizontal axis and in fluid communication allowing lateral flow from section 1 throughout all sections to section 5.

In one embodiment, the kit further comprises a sample collecting instrument.

In one embodiment, the kit comprises at least two sections 4 each one of them comprising different substrates.

In one embodiment, least one of the substrates comprises an active-pixel sensor (APS), an electrode or an excitation device with an active-pixel sensor (APS).

In one embodiment, there is provided a kit for diagnosing an infectious disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
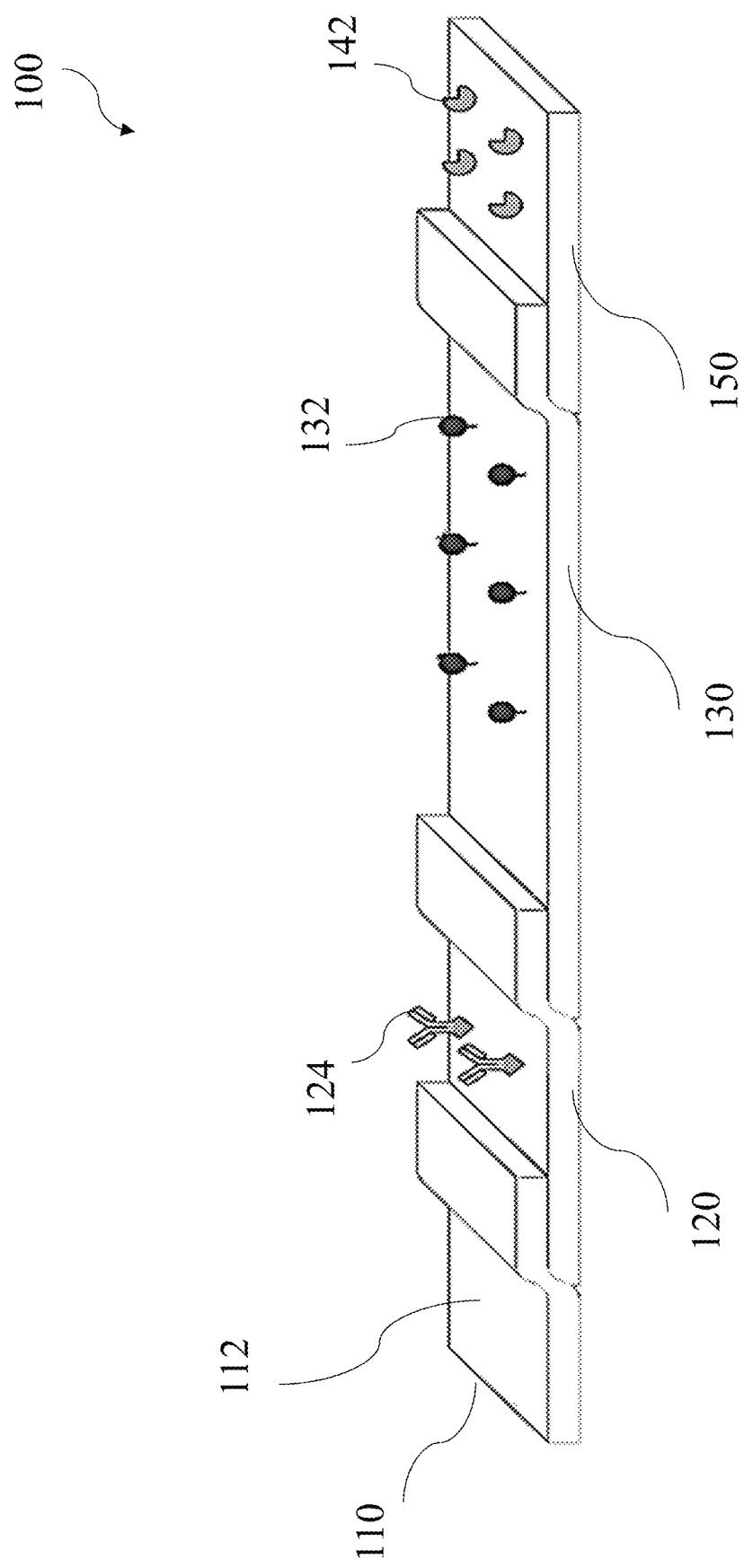
FIG. 1 is a perspective view simplified illustration of a capture flow device, according to some embodiments of the present invention.

The present invention, in some embodiments, relates to a lateral flow device. In some embodiments, the device is a point of care testing device.

According to an aspect of some embodiments of the present invention there is provided a device, comprising at least a section 1, a section 2, a section 3 and a section 4 wherein section 2 is coupled to section 1, section 3 is coupled to section 2 and comprises a surface functionalized with an analyte or equivalent thereof, section 4 is coupled to section 3 and section 1, section 2, section 3 and section 4 are arranged along a horizontal axis and in fluid communication allowing lateral flow from the section 1 throughout all sections to the section 4. In some embodiments, section 1, section 2, section 3 and section 4 are arranged along a horizontal axis, wherein the subsequent section are in fluid communication or are coupled so as to allow a lateral flow from the section 1 throughout all sections to the section 4.

In some embodiments, the term "coupled" as used herein comprises in contact with or in fluid communication. In some embodiments, section 1 comprises a sample collecting surface. In some embodiments, section 2 comprises a surface comprising a recognition molecule having specific affinity to an analyte linked to a reporter molecule, wherein the signal molecule generates a chemically and/or a physically detectable reaction. In some embodiments, section 4 comprises a surface comprising a substrate molecule.

In some embodiments, section 2 comprises a surface in contact with a recognition molecule having specific affinity to the analyte, wherein the recognition molecule is linked or bound to a reporter molecule, and wherein the reporter molecule generates a trigger. In some embodiments, section 4 comprises a surface in contact with a substrate molecule, wherein the substrate molecule generates a signal in response to the trigger generated by the reporter molecule.

In some embodiments, a device according to the present invention further comprises a calibration area. In some embodiments, a device according to the present invention further comprises a calibration area disposed between section 2 and section 3 and wherein the calibration area is in contact with the substrate molecule. In some embodiments, the substrate molecule of section 4 and the substrate molecule of the calibration area are identical.

In some embodiments, a device according to the present invention further comprises a section 5 coupled to and/or in fluid communication with section 4.

In some embodiments, section 1, section 2, section 3 section 4 and section 5 are partially overlapping. In some embodiments, section 1, section 2, section 3 section 4 and section 5 are partially overlapping, wherein overlapping comprises from 0.01% to 99%, from 0.01% to 95%, from 0.01% to 90%, from 1% to 90%, from 0.01% to 1%, from 1% to 80%, from 1% to 70%, from 1% to 60%, from 1% to 50%, from 1% to 40%, from 1% to 30%, from 1% to 20%, from 1% to 10%, from 1% to 5%, from 5% to 10%, from 10% to 20%, from 20% to 30%, from 30% to 40%, from 10% to 30%, from 10% to 40%, from 10% to 50%, from 10% to 60%, from 10% to 70%, of the total surface of the section.

In some embodiments, the terms "in fluid communication", "in contact with" and "coupled" are used herein interchangeably. According to an aspect of some embodiments of the present invention there is provided a device, comprising (i) a section 1 comprising a sample collecting surface, (ii) a section 2 comprising a surface comprising a recognition molecule having specific affinity to an analyte or equivalent thereof linked to a reporter molecule, wherein the signal molecule generates a chemically and/or a physically detectable reaction, (iii) a section 3 comprising a surface functionalized with an analyte or equivalent thereof (iv) section 4 comprising a surface with a substrate molecule deposited thereon, and (v) a section 5 comprising a surface available for holding excess sample, wherein sections 1, 2, 3, 4 and 5 are arranged along a horizontal axis and in fluid communication allowing lateral flow from the section 1 throughout all sections to the section 5.

In some embodiments, there is provided a device for determining the amount of an analyte in a sample. In some embodiments, there is provided a device for quantifying the amount of an analyte in a sample. In some embodiments, there is provided a device for determining and quantifying the amount of an analyte in a sample. In some embodiments the quantitation is relative or absolute.

According to an aspect of some embodiments of the present invention there is provided a lateral flow device. In some embodiments, a device according to the present invention is a point of care testing device.

As used herein, the term "point of care testing" refers to real time diagnostic testing that can be done in a rapid time frame so that the resulting test is performed faster than comparable tests that do not employ this system. It can be performed in a doctor's office, at a bedside, in a stat laboratory, emergency room, ambulances or at home and other such locales, particularly where rapid and accurate results are required. The patient can be present, but such presence is not required. Point of care includes, but is not limited to: emergency rooms, operating rooms, hospital laboratories and other clinical laboratories, doctor's offices, in the field, or in any situation in which a rapid and accurate result is desired.

As used herein the term "lateral flow device" refers to devices that include bibulous or non-bibulous matrices capable of transporting analytes and reagents to a preselected site. Many such devices are known, in which the strip is made of water absorbing materials such as nitrocellulose, paper, cellulose, and other bibulous materials. A test strip used in lateral flow, is a strip in which a test sample suspected of containing an analyte flows through the strip to a detection zone in which the analyte (if present) interacts with a detection agent to indicate a presence, absence and/or quantity of the analyte.

As used herein the term "analyte" refers to a substance to be detected which may be present in a test sample. The analyte can be any substance for which there exists a naturally occurring specific binding member (such as, an antibody or aptamer, DNA, etc.), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs). It is to be understood that the invention can be configured for detecting a broad range of analytes, including therapeutic drugs, drugs of abuse, hormones, vitamins, proteins (including antibodies of all classes), peptides, amino acids, steroids, bacteria, yeast, mold, viruses, parasites, components or products of bacteria, fungi, allergens of all types, antigens of all types, products or components of normal or malignant cells, and the like.

In some embodiments, the analyte comprises a virus. In some embodiments, the analyte comprises a protein. In some embodiments, the analyte comprises biological cells. In some embodiments, the analyte comprises toxins and pathogens. In some embodiments, the analyte comprises pharmaceuticals and drugs.

The term "sample," as used herein, is used in its broadest sense. A "biological sample," as used herein, includes, but is not limited to, any quantity of a substance (analyte molecule) from a living thing or formerly living thing that can be solubilized in a first extraction buffer optionally containing a surfactant or detergent. Such living things include, but are not limited to, mammals, humans, non-human primates, mice, rats, monkeys, dogs, rabbits, and other animals; plants; single celled organisms such as yeast and bacteria and viruses. Such substances include, but are not limited to, physiological liquids, blood, (e.g; whole blood), plasma, serum, urine, amniotic fluid, synovial fluid, endothelial cells, leukocytes, monocytes, other cells, organs, tissues, bone marrow, lymph nodes, and spleen, e.g., from resected tissue or biopsy samples; and cells collected, e.g. by centrifugation, from any bodily fluids; and primary and immortalized cells and cell lines. Samples can include fresh samples and historical samples. However, the term "sample" also includes environmental samples, such as water samples or smear tests of diverse items. As used herein, a "cell based sample" is understood as a sample wherein substantially all (e.g. at least 90%, at least 95%, at least 98%, at least 99%) of the analyte molecule present in the sample for detection is present inside cells of the sample (i.e., not in serum, extracellular fluid, cell culture media). In preferred embodiments, the sample is a liquid sample.

In some embodiments, a sample is selected from water, blood, urine, sweat, saliva, and serum. In some embodiments, a biological sample is obtained from an animal (including mammal). In another embodiment, biological sample is obtained from a human. In another embodiment, biological sample is obtained well within the capabilities of those skilled in the art.

According to an aspect of some embodiments of the present invention there is provided a device which utilize specific binding members (recognition element). The term "specific binding member" as used herein, refers to a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, aptamers, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, protein subunits and complexes thereof, including those formed by recombinant DNA molecules.

The term "substrate molecule" as used herein, refers to molecules that interact specifically with a reporter molecule. By "interacts specifically" it is meant that the substrate molecule exhibits essentially a structural or physical change leading to the generation of a measurable physical signal.

The term "specificity" as used herein, refers to the ability of a binding moiety to bind preferentially to one analyte molecule, versus a different antigen, and does not necessarily imply high affinity (as defined further herein). A binding moiety that can specifically bind to and/or that has affinity for a specific analyte molecule is said to be "against" or "directed against" the antigen or antigenic determinant. A recognition molecule according to the invention is said to be "cross-reactive" for two different analyte molecules if it is specific for both these different analyte molecules.

The term "affinity", as used herein, refers to the degree to which a recognition molecule binds to an analyte molecule so as to shift the equilibrium of free analyte molecule toward the presence of a complex formed by their binding. Thus, for example, where an analyte molecule and recognition molecule are combined in relatively equal concentration, a recognition molecule of high affinity will bind to the available analyte molecule so as to shift the equilibrium toward high concentration of the resulting complex. The dissociation constant (Kd) is commonly used to describe the affinity between the recognition molecule and the its target. In some embodiments, the dissociation constant is lower than $10^{-3}$ M. In some embodiments, the dissociation constant is lower than $10^{-2}$ M. In some embodiments, the dissociation constant is lower than $10^{-4}$ M. In some embodiments, the dissociation constant is lower than $10^{-5}$ M. In some embodiments, the dissociation constant is lower than $10^{-6}$ M. In some embodiments, the dissociation constant is lower than $10^{-7}$ M. In some embodiments, the dissociation constant is lower than $10^{-8}$ M. In some embodiments, the dissociation constant is lower than $10^{-9}$ M.

The terms "specifically bind" and "specific binding", as used herein, refer to the ability of a binding domain to preferentially bind to a particular analyte molecule that is present in a homogeneous mixture of different molecules. In some embodiments, a specific binding interaction will discriminate between desirable and undesirable molecules in a sample, in some embodiments more than about 2 to 100-fold or more (e.g., more than about 1000- or 10,000-fold).

As used herein and in the claims, the term "functionalized surface" refers to a surface of an article that has been modified so that one or a plurality of molecules or functional groups are present thereon. In some embodiments, the plurality of molecules or functional groups are bound to the functionalized surface. The manner of treatment is dependent on, for example, the nature of the chemical compound to be synthesized and the nature and composition of the surface.

As used herein, the term "surface" refers to the material that the sections are made of. In some embodiments, surface is referred to an outer surface. A variety of materials can be used as surface according to the present invention. The materials include any material that can act as a support for attachment of the molecules of interest. Such materials are known to those of skill in this art. These materials include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutylene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media. In some embodiments, the surface comprises a water absorbing material, as described hereinabove.

Device and Assay

Reference is made to FIG. 1, which is a simplified illustration of some of the components of a device 100, according to some embodiments of the invention.

According to some embodiments of the present invention, section 1 110, section 2 120, section 3 130 and section 4 150 are arranged along a horizontal axis and in fluid communication allowing lateral flow from section 1 throughout all sections to section 4.

In some embodiments, section 1 110, section 2 120, section 3 130 and section 4 150 are in contact with each other, so as to allow a lateral flow from section 1 throughout all sections to section 4.

In some embodiments, section 1 110, section 2 120, section 3 130 and section 4 150 are partially overlapping. In some embodiments, overlapping is in the range of 0.01% to 99% of the total surface of a section. In some embodiments, overlapping is in the range of 0.05% to 99%, 0.1% to 99%, 0.1% to 90%, 0.1% to 80%, 0.1% to 70%, 0.1% to 60%, 0.1% to 50%, 0.1% to 40%, 0.1% to 30%, 0.1% to 29%, 0.1% to 10%, or 0.1% to 5% of the total surface of a section, including any range therebetween. In some embodiments, section 1 is partially overlapping above section 2. In some embodiments, section 1 is partially overlapping bellow section 2. In some embodiments, section 2 is partially overlapping bellow section 3. In some embodiments, section 2 is partially overlapping above section 3. In some embodiments, section 3 is partially overlapping above section 4. In some embodiments, section 3 is partially overlapping bellow section 4.

In some embodiments, at least three sections of a device according to the present invention are disposed along more than one plane. In some embodiments, two consecutive sections are disposed along one or more planes. In some embodiments, section 1 110, section 2 120, section 3 130 and section 4 150 share at least one plane. In some embodiments, all sections are disposed along the same plane.

According to some embodiments of the present invention, section 1 110, section 2 120, section 3 130 and section 4 150 serve as solid support onto which different components are either adsorbed or immobilized (such as bound). In some embodiments, section 2 120, section 3 130 and section 4 150 comprise a surface in contact with or bound to the component (such as a substrate molecule, a recognition molecule, or an analyte), wherein the surface is as described hereinabove. In some embodiments, the component on section 2 120, comprise a recognition molecule (such as an immunoreagent) adsorbed, in contact with or bound to the section. In some embodiments, the component on section 2 120, comprise the recognition molecule adsorbed to the section. The component on section 3 130 comprise immunoreagents and are either adsorbed or covalently immobilized (e.g. covalently bound) to the section. In some embodiments, the different components are immobilized prior to the assembly of the sections. In some embodiments, the different components are immobilized after the assembly of the sections.

In some embodiments, section 1 110 comprises a sample collecting surface 112, section 2 120 comprises a surface comprising a recognition-reporter molecule complex 124, section 3 comprises surface functionalized with an analyte 132 and section 4 150 comprises a surface with a substrate molecule deposited thereon 142. In some embodiments, section 3 130 comprises a calibration area 140. In some embodiments, section 3 130, further comprises a calibration area 140 comprising a substrate molecule placed adjacent to section 2 120.

In some embodiments, section 1 110, section 2 120, section 3 130 and section 4 150 comprise a membrane. In some embodiments, a membrane comprises polyester. In some embodiments, a membrane comprises cellulose.

As used herein the term "membrane" refers to a boundary, a layer, barrier, or material, which may, or may not be permeable. The term "membrane" may further refer to an interface. In some embodiments, the terms "membrane" and "surface" are used herein interchangeably. Unless specified otherwise, membranes may take the form a solid, liquid, or gel, and may or may not have a distinct lattice, none cross-linked structure, or cross-linked structure. In some embodiments, the membrane is a fibrous membrane.

In some embodiments, section 1 110, section 2 120, section 3 130 and section 4 150, comprise a matrix. The matrix defines a lateral flow path. In some embodiments, the path is a microfluidic path. In some embodiments, the flow path is axial, and the flow is one way directed. In some embodiments, the flow direction is downstream from section 1. As used herein the term "downstream" refers a location to which fluid applied to the sample collecting surface will flow, such location being opposite direction to section 1. In some embodiments, the dissolved or dispersed components of the liquid sample are carried at substantially equal rates and with relatively unimpaired flow laterally through the matrix. In some embodiments, the lateral flow as used herein, refers to a capillary flow. In some embodiments, the lateral flow is generated by a capillary action. In some embodiments, the dissolved or dispersed components of the liquid sample are modulated by the added PVA membrane and other surface-active materials or ionic buffers forces.

Typical matrix materials that can be used in a device according to the present invention include high density polyethylene, polyvinyl chloride, polyvinyl acetate, copolymers of vinyl acetate and vinyl chloride, polyamide, polycarbonate, nylon, glass fiber, orlon, polyester, polystyrene, cotton, cellulose and the like, or blends. The optimum pore diameter for the membrane for use in the invention is about 20 μm to about 140 μm. Other materials, such as untreated paper, nitrocellulose, derivatized nylon, cellulose and the like may also be used according to the present invention.

In some embodiments, the matrix or the membrane comprises a hydrophilic material. In some embodiments, the hydrophilic material is a hydrophilic polymer. In some embodiments, the matrix or the membrane comprises a polymer wettable by an aqueous solution.

Figure 2A:
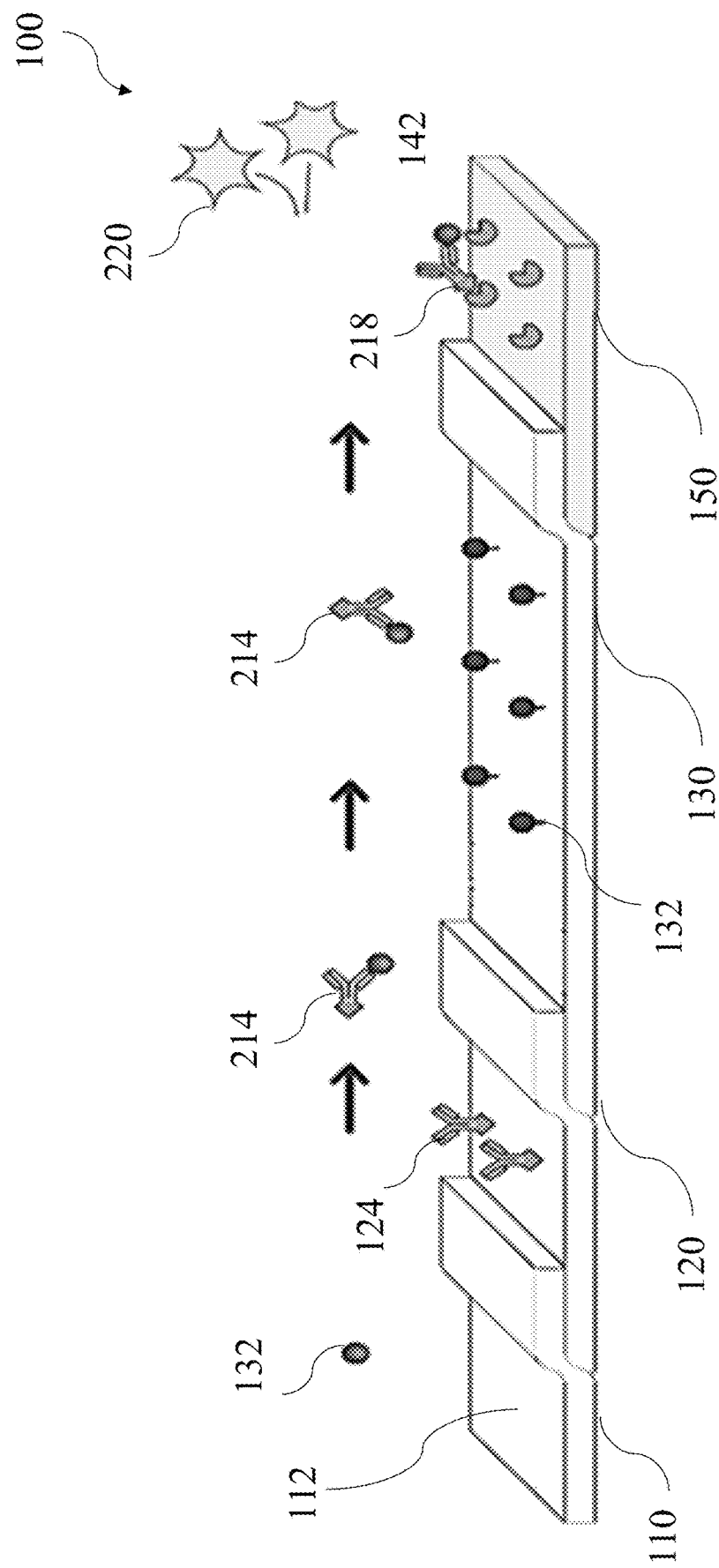
FIGS. 2A-B are perspective view simplified illustrations of how the capture flow device works during an assay measurement according to some embodiments of the present invention; with an analyte present in a sample (FIG. 2A), and with an analyte absent from a sample (FIG. 2B)

Reference is now made to FIG. 2, which is a simplified illustration of how a device 100 works during an assay measurement according to some embodiments of the present invention. In some embodiments, the device comprises a section 1 110 with a sample collecting surface 112, a section 2 120 comprising a surface with a recognition molecule 124 linked to a reporter molecule, a section 3 comprising surface functionalized with an analyte 132 and section 4 150 comprising a surface with a deposited substrate molecule 142.

There are two main possibilities that can happen during measurements. A first possibility is represented FIG. 2A. In some embodiments, a liquid sample with a target analyte 132 is placed in section 1 110. The sample migrates to section 2 120, via lateral flow, where it encounters the recognition molecule 124. A complex 214 is formed based on molecular recognition (such as affinity-based interaction or binding between the recognition molecule and the analyte), wherein complex 214 comprises the analyte 132 bound or in contact with the recognition molecule 124, and wherein the recognition molecule 124 is bound to a reporter molecule generating a trigger. The analyte-recognition-reporter molecule complex 214 formed, continues to migrate via lateral flow to section 3 130 comprising the analyte 132. Since the analyte-recognition molecule complex 214 was already formed, the complex 214 can't be immobilized in section 3 130 and will continue and migrate to section 4 150 comprising a surface with the deposited substrate molecule 142. Here, the complex 214 or the trigger generated by the reporter molecule will interact with the substrate molecule 142. The interaction 218 formed will result in a reaction, thereby generating a signal 220, and confirming the presence of the analyte in the sample in an absolute manner. The type of signal generation will depend on the reporter molecule used that is conjugated to the reporter molecule and the substrate molecule deposited in section 4 150.

Figure 2B:
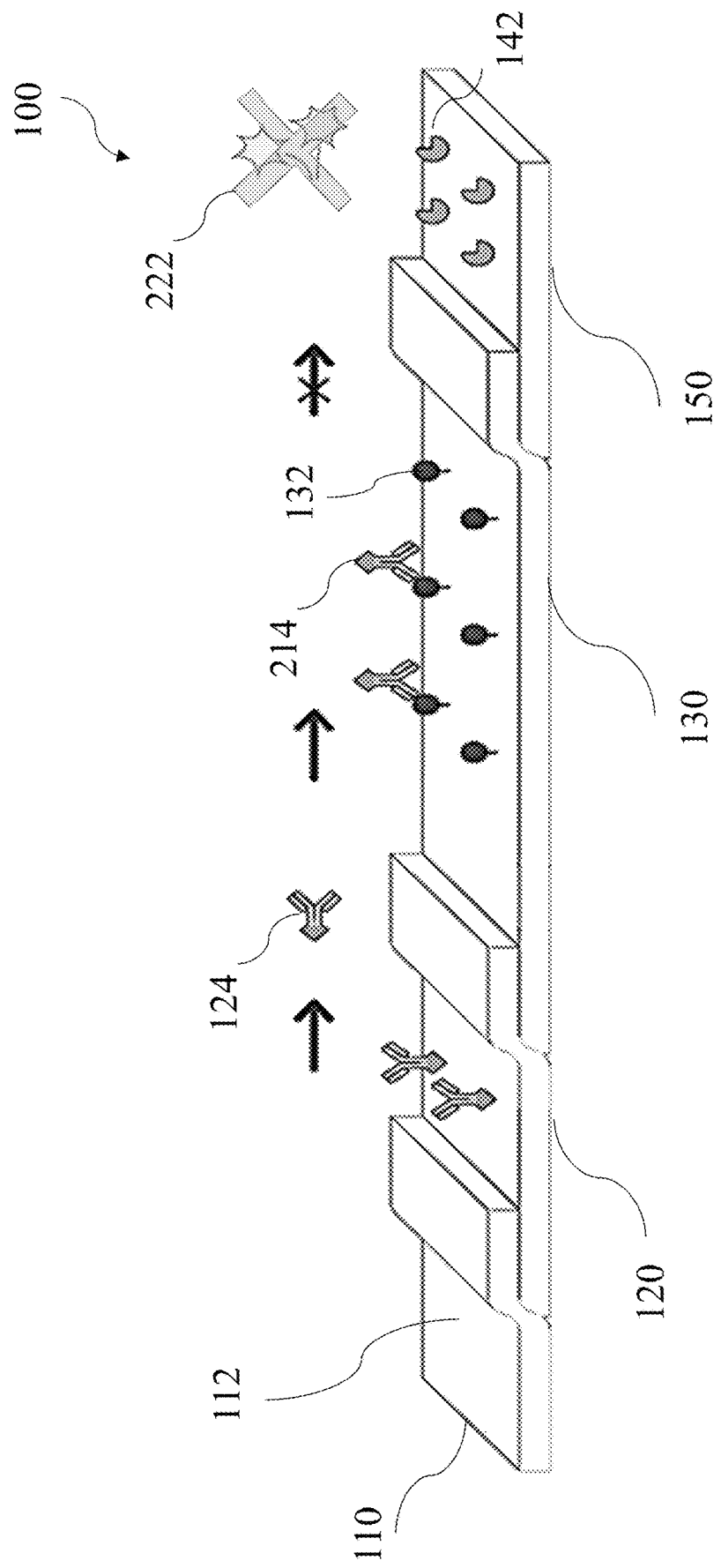

Reference is now made to FIG. 2B. In some embodiments, in the case of a sample without a target analyte 132, the sample migrates from section 2 120, via lateral flow, where it encounters the recognition molecules 124. The reporter molecules will then migrate unbound with the sample to section 3 130, where they will be linked to the analyte 132, forming the complex 214 and stopped from migrating further to the next section 4 150, thus no visible signal will be observed in section 4 150 (as exemplified in FIG. 2B by the cross 222).

In some embodiments, section 1 110, section 2 120, section 3 130 and section 4 150, are arranged in such way that section 3 130 is able to receive both analyte-recognition-reporter molecule complex 214 and excess of free reporter molecules 124 and section 4 150 is able to receive only analyte-recognition-reporter molecule complex 214. In some embodiments, section 3 130 comprising an analyte 132, positioned between section 2 120 and section 4 150, ensures that only analyte-recognition-reporter molecule complex 214 migrates to section 4 150.

In some embodiments, section 1 110, section 2 120, section 3 130 and section 4 150, are in fluid communication, allowing lateral flow from section 1 to section 2, from section 2 to section 3, and from section 3 to section 4.

Calibration Area

In some embodiments, a device according to the present invention further comprises a calibration area.

In some embodiments, a device according to the present invention further comprises a calibration area positioned between section 2 and section 3 and comprising a substrate. In some embodiments, calibration area is in fluid communication with or is coupled to section 2 and section 3.

Figure 3:
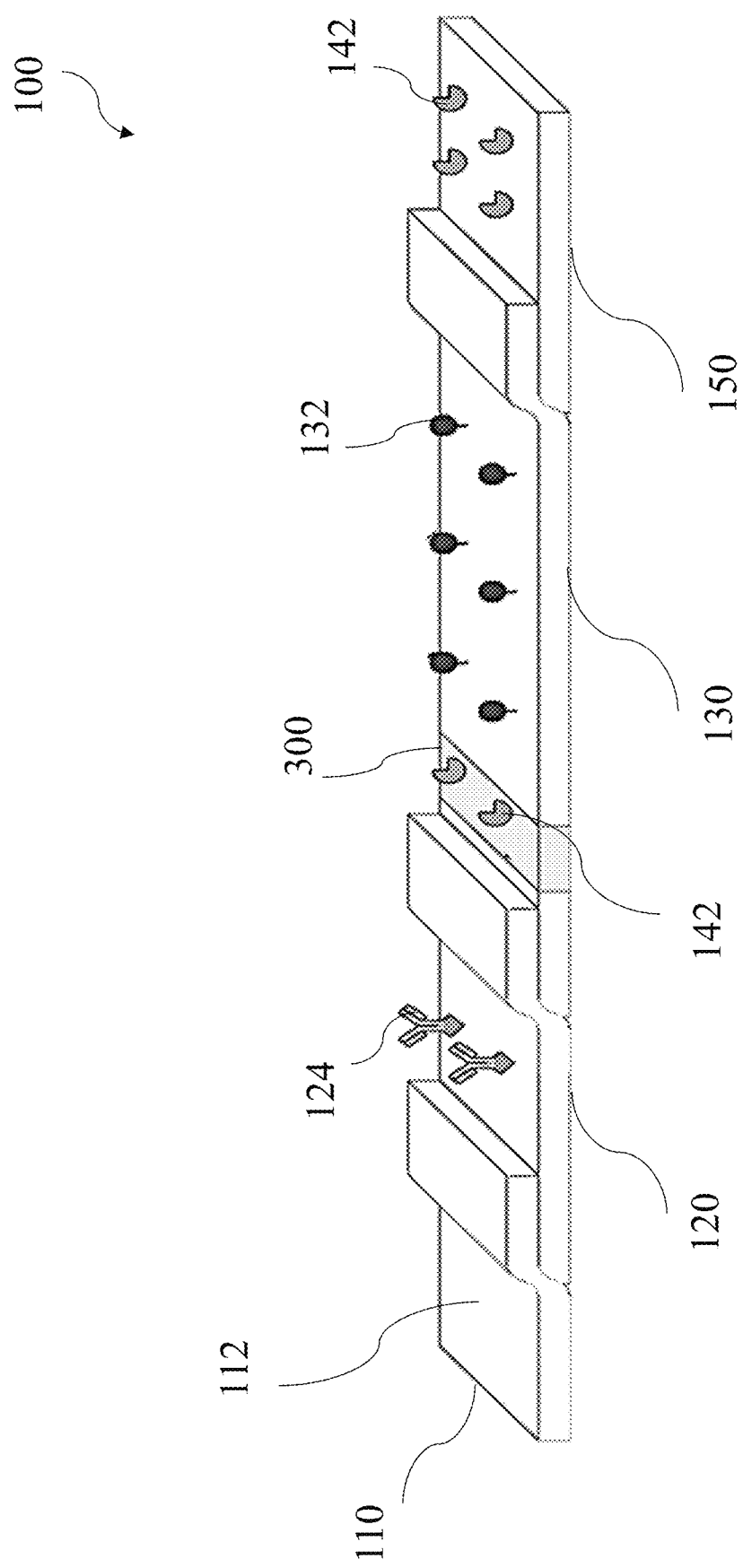
FIG. 3 is a perspective view simplified illustration of a device comprising a calibration area, according to some embodiments of the present invention.

Reference is now made to FIG. 3 is a simplified illustration of a device 100 according to the present invention comprising a calibration area 300, according to some embodiments of the invention.

In some embodiments, a calibration area 300 comprising a substrate molecule 142 is placed adjacent to section 2 120. In some embodiments, a calibration area 300 is in fluid communication with or coupled to section 2 120.

There are two main possibilities that can happen during measurements in a device 100 comprising a calibration area 300, according to some embodiments, of the invention.

Figure 4A:
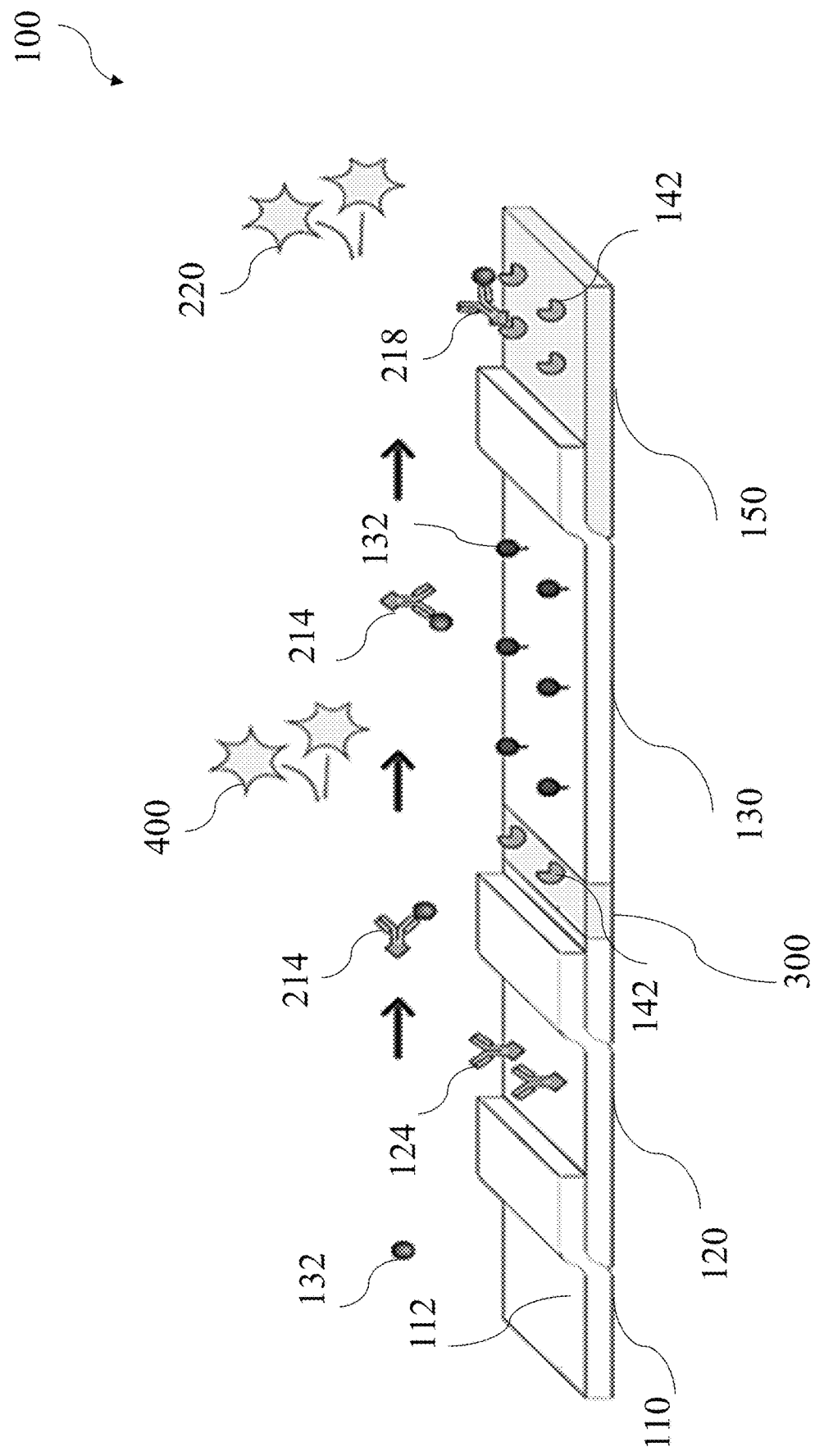
FIGS. 4A-B are perspective view simplified illustrations of how the device comprising a calibration area works during an assay measurement according to some embodiments of the present invention with an analyte present in a sample (FIG. 4A), and with an analyte absent from a sample (FIG. 4B)

A first possibility is represented FIG. 4A. In some embodiments, a liquid sample with a target analyte 132 is placed in section 1 110. The sample migrates to section 2 120, via lateral flow, where it encounters the recognition molecules 124. A complex 214 is formed based on molecular recognition. The analyte-recognition-reporter molecule complex 214 formed, continues to migrate via lateral flow to calibration area 300 comprising a substrate molecule 142. The substrate molecule 142 is able to produce a first signal 400 when oxidized by both the reporter in the analyte-recognition-reporter molecule complex 214 and if present, the reporter in the recognition-reporter molecule complex 124, thereby indicating the proper function and total quantity of the reporter molecule 124 and the reported molecule 214 entering section 3 130. The signal 400 produced, can also be used for signal calibration. Signal calibration can be done by measuring (using photodetector, cellphone, potentiostat (electrochemical signal, fluorescent measuring device, camera) and correlating signal intensity with concentration of a recognition-reported molecule complex entering section 3 130.

The analyte-recognition-reporter molecule complex 214 formed, continue in a lateral flow, is not able to bind to the analyte 132 immobilized in section 3 130, and therefore will continue and migrate to section 4 150 comprising a surface with the deposited substrate molecule 142. The complex, containing reporter oxidizes the substrate molecule thereby triggering a reaction and generating a second signal 220. The type of signal generation will depend on the signal molecule used (reporter molecule and substrate molecule).

Figure 4B:
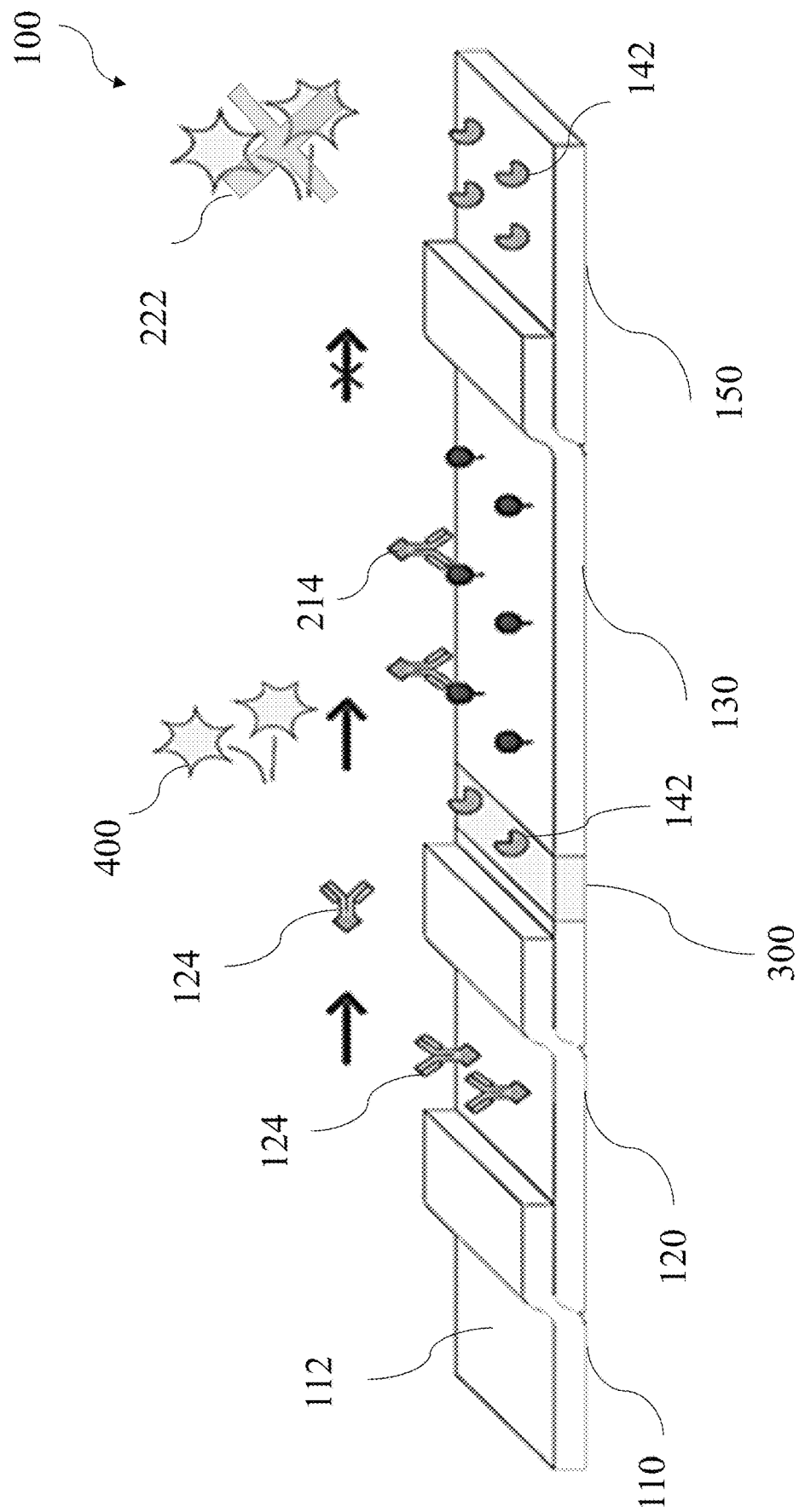

Reference is now made to FIG. 4B. In some embodiments, in the case of a sample without a target analyte 132, the sample migrates from section 2 120, via lateral flow, where it encounters the recognition-reporter molecules 124. The recognition-reporter molecules will then migrate unbound with the sample to calibration area 300 as described herein. Also in this case, a signal 400 is generated, thereby indicating the proper function and quantity of the recognition-reporter molecule 124. The recognition-reporter molecules will continue to migrate to section 3 130, where they will be linked to the analyte 132 and stopped from migrating further to the next section 4 150, thus no visible signal will be observed in section 4 150 (as exemplified in FIG. 4B by the cross on top of the signal 222).

In some embodiments, the calibration area 300 is designed to receive both analyte-recognition-reporter molecule complex 214 and excess of free recognition-reporter molecules 124. In some embodiments, the calibration area 300 is designed to receive a trigger generated by the reporter molecule, so as to form a detectable signal. In some embodiments, section 4 150 is designed to receive only analyte-recognition-reporter molecule complex 214. In some embodiments, section 4 150 is designed to receive only the trigger generated by the reporter molecule. In some embodiments, section 4 150 is designed to receive only recognition-reporter molecule complex 124.

In some embodiments, section 1 110, section 2 120, section 3 130 and section 4 150, are arranged in such way that section 3 130 is able to receive both analyte-recognition-reporter molecule complex 214 or the trigger and excess of free recognition-reporter molecules 124 and section 4 150 is able to receive only analyte-recognition-reporter molecule complex 214 or the trigger. In some embodiments, section 3 130 comprising an analyte 132, positioned between section 2 120 and section 4 150, ensures that only analyte-recognition-reporter molecule complex 214 or the trigger migrates to section 4 150.

In some embodiments, section 1 110, section 2 120, section 3 130 and section 4 150, are in fluid communication.

In some embodiments, a device as described herein comprises calibration area comprising a substrate molecule, wherein the calibration area is placed adjacent to section 2. In some embodiments, a device as described herein comprises calibration area comprising a substrate molecule placed between section 2 and section 3. In some embodiments, the calibration area comprises a membrane, wherein the membrane is as described hereinabove.

In some embodiments, the calibration area is placed before the surface functionalized with an analyte. In some embodiments, the calibration area is devoid of the analyte. In some embodiments, the calibration area is devoid of a recognition molecule. In some embodiments, the calibration area is devoid of a reporter molecule. In some embodiments, when the substrate molecule of the calibration area encounters a reporter molecule, the reporter molecule generates a trigger, that upon interaction with the substrate molecule generates a signal giving an indication for the functionality and quantity of the reporter molecule and a reference of total signal intensity. In some embodiments, the signal intensity is used for signal calibration.

In some embodiments, the substrate molecule is in contact with the surface of the calibration area. As used herein, "in contact" may be referred to bound via a covalent or a non-covalent bond. In some embodiments, a substrate molecule is a color producing signal substrate molecule such as 5-Bromo-4-Chloro-3-IndolylPhosphate (BCIP), 3, 3', 5, 5'-tetramethylbenzidine (TMB), p-Nitrophenyl Phosphate, Disodium Salt (PNPP), 2,2'-Azinobis [3-ethylbenzothiazoline-6-sulfonic acid]-diammonium salt (ABTS), o-phenylenediamine dihydrochloride (OPD). In some embodiments, a substrate molecule is a light producing signal substrate molecule such as 1,2-Dioxetane (CDP-star and CSPD).

Section 1

In some embodiments, a device as described herein comprises a section 1, comprising a sample collecting surface.

In some embodiments, a collecting surface is a filter. In some embodiments, a collecting surface is a solid support that may hold the sample. In some embodiments, a collecting surface comprises a membrane or matrix, wherein the membrane or matrix is as described hereinabove.

In some embodiments, a collecting surface comprises a material capable of absorbing or adsorbing a liquid sample.

In some embodiments, the size and shape of section 1 is not critical and it may vary.

In some embodiments, the sample collecting surface is comprised of filter for whole cell and large bodies filtration.

In some embodiments, the sample collecting surface contains a buffer for controlling pH and ionic strength.

As used herein the term "sample collecting surface" refers to a surface wherein the sample is applied. The applied sample migrates consecutively from the sample collecting surface in section 1 to section 2, section 3, and section 4 in this specific order.

Section 2

In some embodiments, a device as described herein comprises a section 2, comprising a surface comprising a recognition molecule linked or bound to a reporter (signal) molecule. In some embodiments, section 2, comprises a surface comprising a deposited recognition molecule linked to a reporter (signal) molecule. In some embodiments the recognition molecule has specific affinity to the analyte. In some embodiments, the reporter molecule generates a chemically and/or a electric and/or a fluorescent and/or a physically detectable reaction. In some embodiments, the reporter molecule generates a trigger. In some embodiments, the recognition molecule is dried on the surface of section 2. In some embodiments, the recognition molecule is unbound to the surface of section 2. In some embodiments, the trigger induces a signal formation upon contacting the substrate molecule. In some embodiments, the trigger is capable to interact chemically (e.g. via a reaction and/or a non-covalent binding), physically (e.g. via photon-induced excitation, via interactions with ionizing radiation, or by inducing electromagnetic field-based interaction). In some embodiments, the trigger comprises at least one of: a reactive compound (such as a peroxide, or any compound capable of reacting with the substrate molecule so as to generate a signal), an electromagnetic radiation, an ionizing radiation, and a charged particle or a combination thereof. In some embodiments, the trigger is a photon having a wavelength sufficient to induce a fluorescence, a luminescence, a phosphorescence or a colorimetric reaction of the substrate molecule.

The term "recognition molecule" as used herein refers to a molecule possessing a high affinity to (i.e., an equilibrium dissociation constant values of $K_d \leq 10^{-9}$ M), in a biologically relevant system (e.g., in vitro, ex vivo or in vivo). In some embodiments, the "recognition molecule" comprises a "reporter molecule". In some embodiments, the "recognition molecule" comprises a "reporter molecule" which is capable of generating and generates a measurable signal detectable by external means.

The term "reporter molecule" as used herein refers to a chemical group or a molecular motif possessing medium to high affinity towards a molecular reagent or a biomolecule that induces or mediates a reaction that yields a product, that can be monitored instrumentally. In some embodiments, "reporter molecule" include chromogens, catalysts such as enzymes, luminescent compounds such as fluorescein and rhodamine, chemiluminescent compounds such as dioxetanes, acridiniums, phenanthridiniums and luminol, radioactive elements, electroactive compounds, TEMPO, 1,4,5,8-naphthalenetetracarboxylic diimide (NTCDI), and direct visual labels. The selection of a particular reporter molecule is not critical, but it will be capable of producing a signal either by itself or in interaction with one or more additional substances.

Examples of reporter enzymes which can be used to practice the invention include hydrolases, lyases, oxidoreductases, transferases, isomerases and ligases. Some preferred examples are glucose oxidase, phosphatases, esterases, glycosidases and peroxidases. In some embodiments, the reporter molecule is selected from the group consisting of protein, enzyme, horseradish peroxidase, nucleotide, dye, quantum dot, fluorophores, gold, silver and platinum. In some embodiments, the reporter molecule generates a chemically active trigger such as hydrogen peroxide, which oxidizes the substrate molecule.

In some embodiments, a reporter molecule is selected from an enzyme, luminescent substrate compound, fluorescent, electrochemical active compound, fluorophores (organic, quantum dots, fluorescent proteins), organic dye, magnetic particles, gold particles.

In some embodiments, a recognition molecule is selected from DNA, proteins, antigen, bioreceptors, aptamers, phage displayed epitopes, biomimetics, peptide, nucleic acid or antibodies linked to some reporters.

In some embodiments, the recognition element at section 120 is allowed to flow with the sample. The substrate molecule (both on section 300 and 150), and capture element stay in place during the assay time.

Section 3

In some embodiments, a device as described herein comprises a section 3 comprising a surface functionalized with an analyte or equivalent thereof, wherein the surface is as described hereinabove. In some embodiments, the analyte or equivalent thereof is bound to the surface of section 3.

In some embodiments, if a sample without an analyte is used, during the migration, of the sample, the excess of free recognition-reporter molecules will be conjugated into the section 3 functionalized with the analyte or equivalent thereof and won't migrate further to section 4.

In some embodiments, if a sample with an analyte is used, since the analyte-recognition-reporter molecule complex is formed before section 3, the sample will continue and migrate to section 4 comprising a surface with a deposited substrate molecule, thereby generating a signal. The type of signal generation will depend on the reporter molecule used that is conjugated to the recognition molecule and/or the substrate molecule deposited.

In some embodiments, an equivalent to the analyte is used. In some embodiments, an equivalent to the analyte refers to an analogous molecule. An equivalent to the analyte is a molecule with interaction to the same active site on the recognition molecule. In some embodiments, an analyte analog can be a synthetic peptide or a peptide-displaced phage or a subunit of a protein.

Section 4

In some embodiments, a device according to the present invention, comprises a section 4 comprising a surface in contact or bound to a substrate molecule, wherein the surface is as described hereinabove. In some embodiments, section 4 comprises the same substrate molecule as present in the calibration area as described elsewhere herein.

In some embodiments, section 4 comprises a surface comprising electrodes. In some embodiments, section 4 comprises a surface in contact with or bound to a substrate molecule selected from a fluorophore, a luminophore, a photoluminophore, a radioluminescent material, and a light-reactive material or a combination thereof. In some embodiments, the substrate molecule comprises a molecule capable of reacting with peroxide, so as to form a detectable signal.

In some embodiments, when the substrate molecule of section 4 encounters a reporter molecule it is able to emit a signal with a certain intensity. In some embodiments, the signal intensity is compared to the signal obtained from calibration area and used for signal calibration. In some embodiments, the signal obtained is proportional to the analyte concentration in the sample. In some embodiments, the signal obtained is proportional to the analyte concentration in the sample and the time from the sample reaching section 4 to the time of measurement. In some embodiments, the ratio between the signal obtained from the calibration area and section 4, is used as internal standard.

In some embodiments, the signal ratio between the calibration area and section 4, can be compared to predetermined values and can indicate the amount of an analyte present in a sample. In first encounter of the reporter to first substrate molecule zone, a signal proportional to the number of reporter molecules passing by is obtained. Thereafter when those reporter-analyte complexes do not bind to the capture layer, they reach the second area with substrate molecule at the far end and again the reporter marker will oxidize those substrate molecules anew. In case very little analyte is present then first signal is much higher than downstream signal. In case of saturation (or close to saturation of) reporter molecule to analyte then the upstream and downstream signals are close to unit.

Referring to FIG. 4, in some embodiments, when there is no analyte in the sample, the signal ratio between section 4 and the calibration area value is 0. In some embodiments, when there is analyte in the sample, the signal ratio between section 4 and the calibration area value is increasing in correlation with analyte concentration and time from when the sample reach section 4.

In some embodiments, when there is no analyte in the sample, the signal ratio between section 4 and the calibration area value is 0. In some embodiments, when there is analyte in the sample, the signal ratio between section 4 and the calibration area value is between 0 and 1 in correlation to analyte concentration in the sample creating a relative signal.

In some embodiments, the substrate molecule is a colorimetric agent. In some embodiments, the substrate molecule is capable of reacting with the trigger (such as a peroxide) to result in color change. In some embodiments, the substrate molecule is a color producing substrate molecule such as 5-Bromo-4-Chloro-3-IndolylPhosphate (BCIP) or 3, 3', 5, 5'-tetramethylbenzidine (TMB), 4-CN DAB, chromogenic.

In some embodiments, the type of signal depends on the chosen reporter molecule and/or substrate molecule.

In some embodiments, signal detection, quantification or both is done using a reader or detection unit. In some embodiments, the device of the invention further comprises a detection unit. In some embodiments, the detection unit is in operable communication with the device. In some embodiments, the detection unit is in operable communication with section 4. In some embodiments, the detection unit is configured to detect the signal generated by the substrate molecule. In some embodiments, the detection unit comprises electric circuitry.

As used herein, the term "detection unit" refers to an instrument capable of detecting and/or quantitating data, such as on the sections described herein. The data may be visible to the naked eye but does not need to be visible. In some embodiments, the detection unit is in operable communication with a processor. A processor is of a general purpose computer, special purpose computer, or other programmable data processing apparatus to produce a machine, such that the instructions, which execute via the processor of the computer or other programmable data processing apparatus, create means for implementing the functions of the device. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the device. In some embodiments, the signal received form the device is processed by a software so as to generate an output, such as a positive or a negative reporting.

In some embodiments, the program code is excusable by a hardware processor.

In some embodiments, the hardware processor is a part of the control unit.

In some embodiments, there is further provided a read-out of the assay carried out in the device may be detected or measured using any suitable detection or measuring means known in the art. The detection means may vary depending on the nature of the read-out of the assay. In some embodiments, disclosed device also relates to an apparatus including the device in any embodiments thereof, and a detection unit as described herein.

In some embodiments, the detection unit provides a positive reporting. In some embodiments, the detection unit provides a negative reporting. As used herein "positive reporting" refers to an increase in the detection signal with the increase of analyte concentration. As used herein the term "negative reporting" refers to no detection signal.

In some embodiments, a reader is an electrochemical detection unit. In some embodiments, a reader is a colorimetric detection unit. In some embodiments, a detection unit comprises a photodetector such as PhotomultiplierTubes (PMTS), CCD camera or complementary MOS (CMOS). In some embodiments, a detection unit is a cellphone. In some embodiments, a detection unit will include light source for excitation of a fluorescent reporter molecule and a photo detector. In some embodiments, a detection unit is a human.

In some embodiments, a signal is a color change. In some embodiments, a signal is light generation. In some embodiments, a signal is an electron flow. In some embodiments, a signal is an excited light source.

As used herein, the term "color" refers to the relative energy distribution of electromagnetic radiation within the visible spectrum. Color can be assessed visually or by using equipment, such as a photosensitive detector.

As used herein, the term "color change" refers to a change in intensity or hue of color or may be the appearance of color where no color existed or the disappearance of color.

In some embodiments, section 4 further comprises an active-pixel sensor (APS) or an electrode.

Section 5

Figure 5:
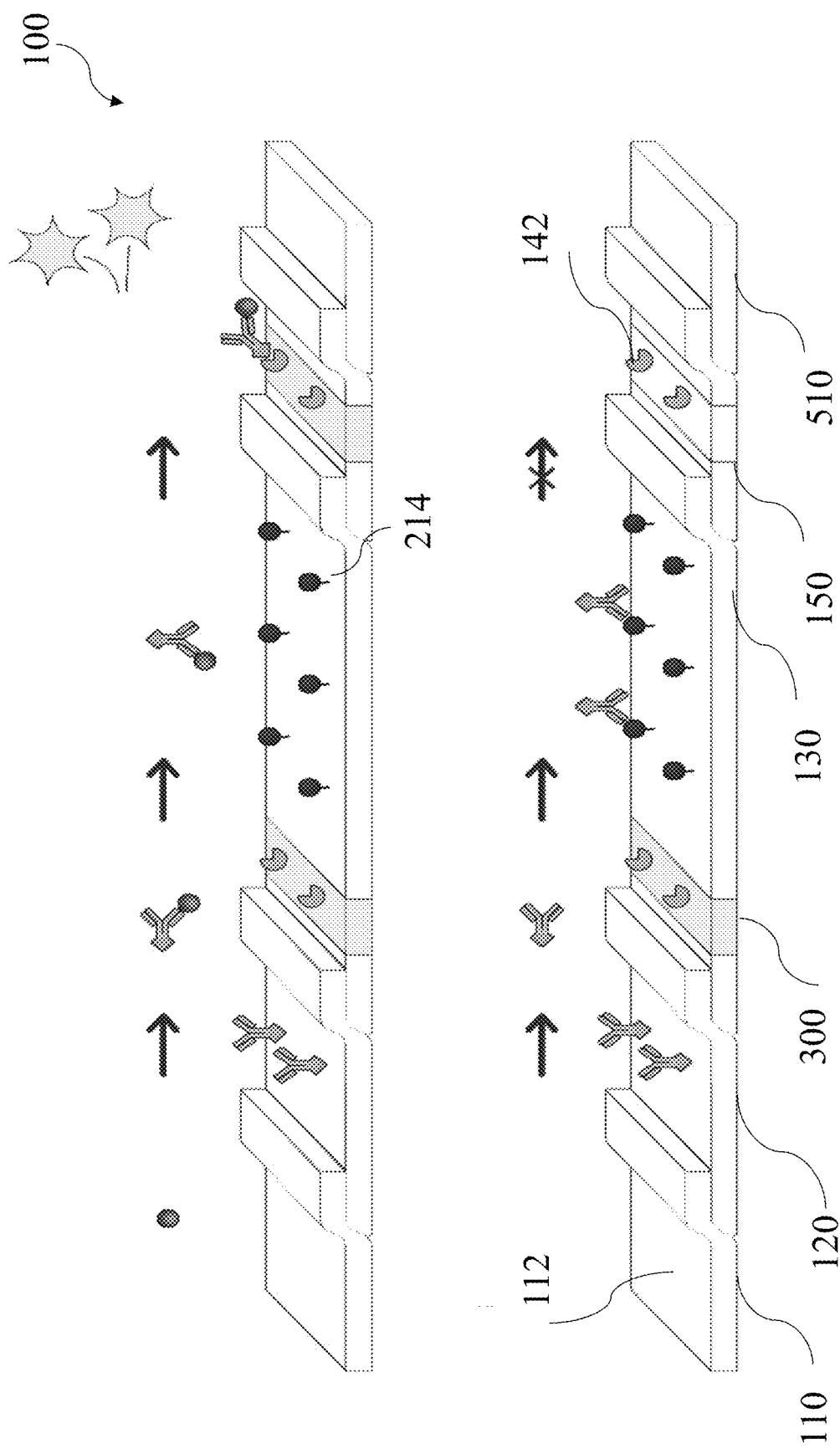
FIG. 5 is a perspective view simplified illustration of a device comprising a section 5, according to some embodiments of the present invention.
Figure 6A:
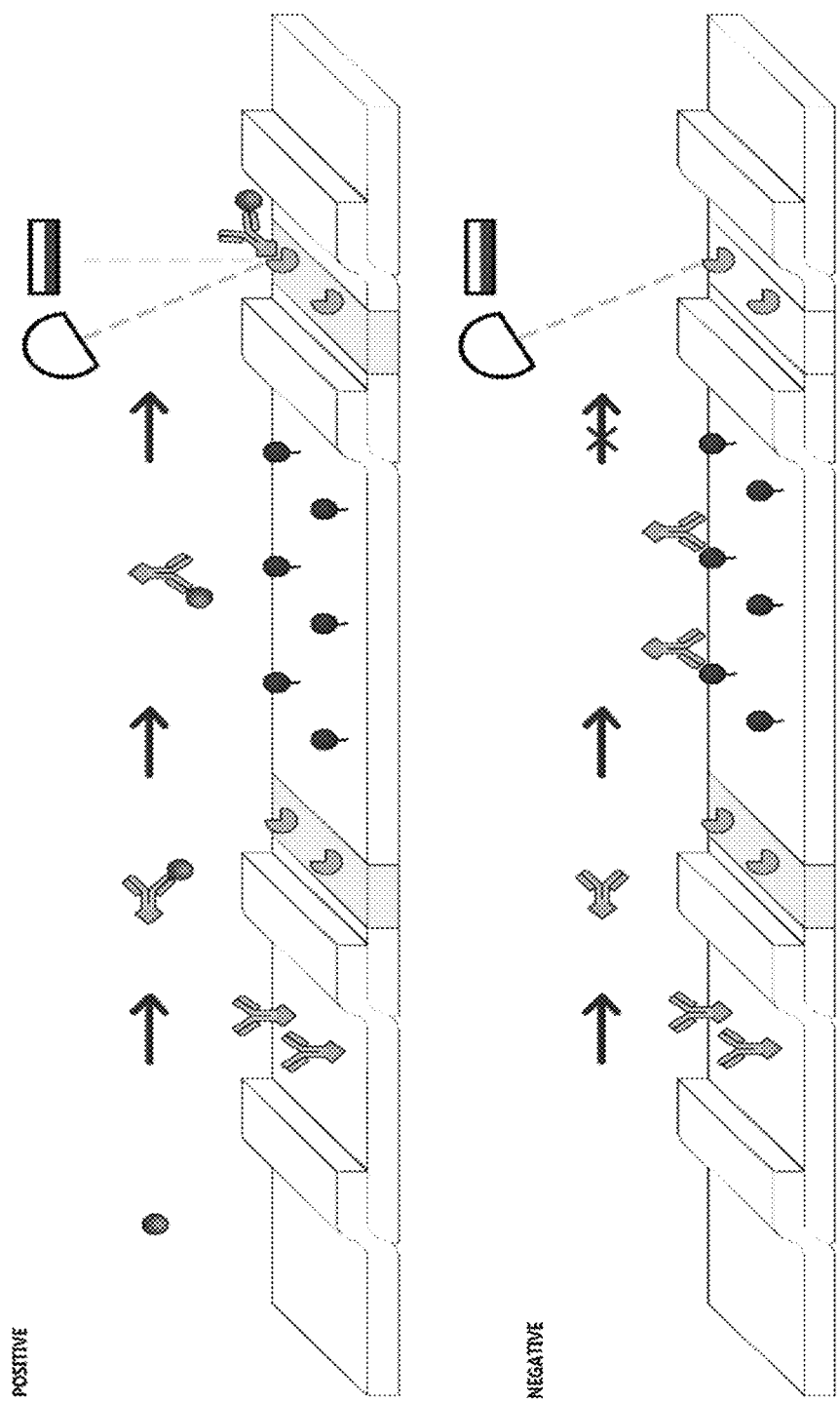
FIGS. 6A-B are perspective view simplified illustrations of a device based on fluorescent signal (FIG. 6A) and based on electrochemical or magnetic signal (FIG. 6B); as the sample migrate through the setup it interacts with the reagents in the sections along the flow path. In case analyte an analyte is present in the sample (positive) it will attach to the recognition molecule and pass through the capture layer, as an analyte-recognition-reporter complex, to the second measurement section where an excitation device will excite the reporter particle and a photodetector will measure the presence of the excited particles during migration through the section to the last section that is used as a reservoir for absorption of the sample (FIG. 6A) or an electrode will measure the presence of the electroactive or magnetic reporter during migration through the section to the last section that is used as a reservoir for absorption of the sample (FIG. 6B). In the case there is no analyte present in the sample (negative) the recognition-reporter molecule will be captured by the pre-immobilized-analyte-like molecule in the capture layer, thus a false signal is prevented in the second substrate-containing section. In both cases, all recognition-reporter molecules that are being released from the second section will register their activity in a calibration line between section 2 and section 3, in the first measuring section, containing both excitation and photodetection device (FIG. 6A) or comprising of electrodes (FIG. 6B). A ratio between the two measurement sections is calculated to determine the amount of analyte-recognition-reporter complex created and reaching the last section. When the flow rate is constant in the setup, the ratio between the signal sections will range between 0 and 1.
Figure 6B:
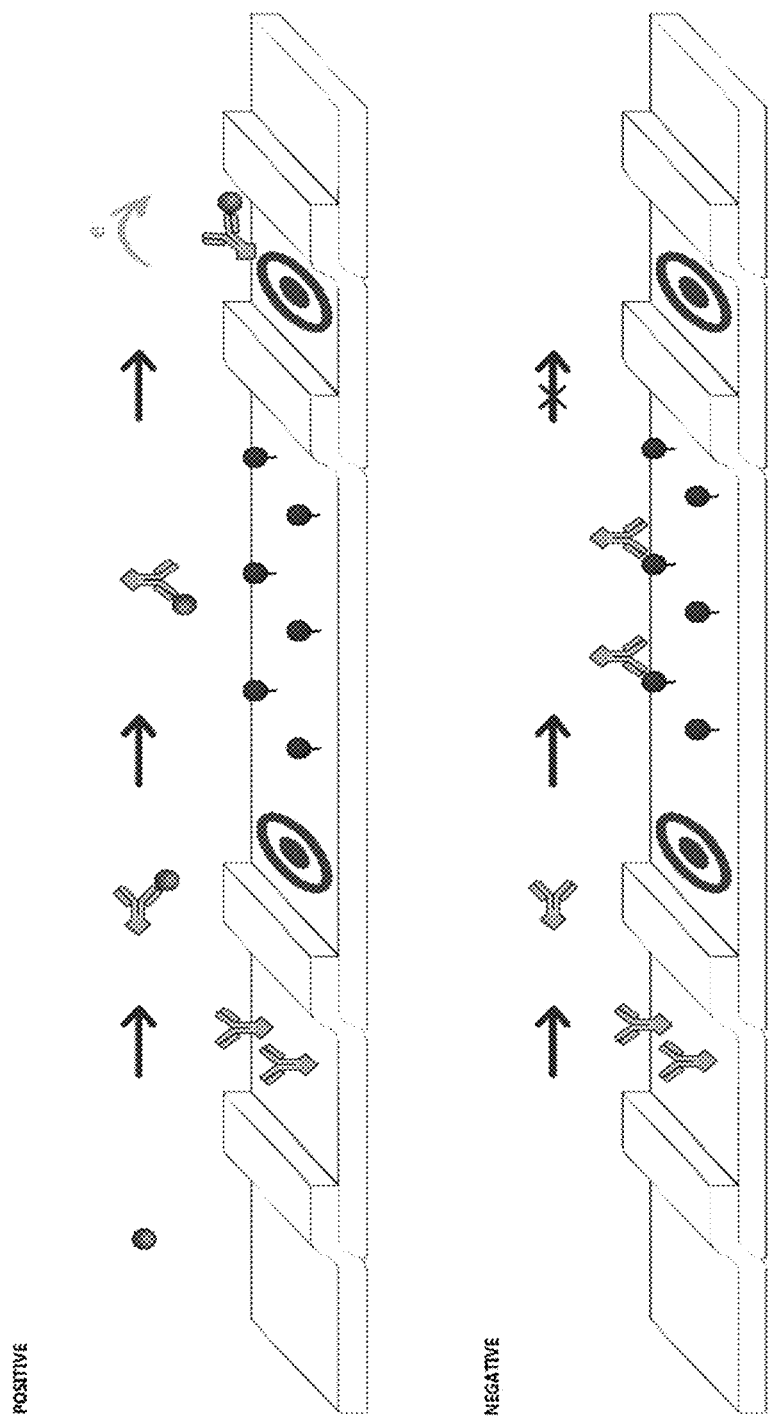

Reference is now made to FIG. 5. According to some embodiments of the present invention, the device further comprises a section 5. In some embodiments, section 5 is coupled to section 4 and in fluid communication with section 4. In some embodiments, there is provided a device comprising a section 1 110, section 2 120, section 3 130, section 4 150 and section 5 510 arranged along a horizontal axis and in fluid communication allowing lateral flow from section 1 throughout all sections to section 5.

In some embodiments, section 5 510 is devoid of reagents and is able to contain the whole sample volume.

Referring to FIG. 5, when the sample reach section 4 150, the reporter will interact with the substrate molecule to give a measurable signal, then continue in migration to section 5 510 to be absorbed.

In some embodiments, there are diffusible membranes between sections of the device, which modulate sample flow rate and interaction time between reagents during measurement procedure.

In some embodiments, a diffusible membrane is made of PolyVinyl Alcohol, paraffin.

In some embodiments, the device will be introduced to vibrations with frequency ranging between 0.1 kHz and 1000 kHz, the vibration will encourage interactions between reagents and increase efficiency. In some embodiments, the vibrations are originating from an internal section. In some embodiments, the vibrations are originating from an external device.

In some embodiments, the flow can be modulated using a magnetic field.

In some embodiments, a device according to the present invention, is capable of detecting lower amounts of an analyte in a sample when compared to a typical enzyme-linked immunosorbent assay (ELISA).

In some embodiments, a device according to the present invention detects the presence of an analyte in a solution with a concentration lower than 25 ng mL$^{-1}$. In some embodiments, a device according to the present invention detects the presence of an analyte in a solution with a concentration lower than 25 ng mL$^{-1}$, lower than 24 ng mL$^{-1}$, lower than 20 ng mL$^{-1}$, lower than 15 ng mL$^{-1}$, lower than 10 ng mL$^{-1}$, lower than 8 ng mL$^{-1}$, lower than 7 ng mL$^{-1}$, or lower than 5 ng mL$^{-1}$, including any value therebetween.

In some embodiments, the ratio of a reporter molecule in section 2 and an analyte in section 3 is in the range of 1:1 to 1:20. In some embodiments, the ratio of a reporter molecule in section 2 and an analyte in section 3 is in the range of 1:2 to 1:20, 1:3 to 1:20, 1:4 to 1:20, 1:8 to 1:20, 1:10 to 1:20, 1:12 to 1:20, or 1:15 to 1:20, including any range therebetween.

In some embodiments, the ratio of a reporter molecule in section 2 and a substrate molecule in calibration area is in the range of 1000:1 to 1:1000. In some embodiments, the ratio of a reporter molecule in section 2 and a substrate molecule in calibration area is in the range of 900:1 to 1:1000, 500:1 to 1:1000, 300:1 to 1:1000, 100:1 to 1:1000, 50:1 to 1:1000, 25:1 to 1:1000, 1000:1 to 1:900, 1000:1 to 1:500, 1000:1 to 1:300, 1000:1 to 1:100, 1000:1 to 1:50, or 1000:1 to 1:25, including any range therebetween.

In some embodiments, the ratio of a reporter molecule in section 2 and a substrate molecule in section 4 is in the range of 1:1 to 1:1000. In some embodiments, the ratio of a reporter molecule in section 2 and a substrate molecule in section 4 is in the range of 1:1 to 1:900, 1:1 to 1:700, 1:1 to 1:500, 1:1 to 1:200, 1:1 to 1:100, 1:1 to 1:50, 1:1 to 1:25, or 1:1 to 1:10, including any range therebetween.

In some embodiments, the ratio of a substrate molecule in calibration area and a substrate molecule in section 4 is in the range of 1:1000 to 1000:1. In some embodiments, the ratio of a substrate molecule in calibration area and a substrate molecule in section 4 is in the range of 900:1 to 1:1000, 500:1 to 1:1000, 300:1 to 1:1000, 100:1 to 1:1000, 50:1 to 1:1000, 25:1 to 1:1000, 1000:1 to 1:900, 1000:1 to 1:500, 1000:1 to 1:300, 1000:1 to 1:100, 1000:1 to 1:50, or 1000:1 to 1:25, including any range therebetween.

The Method

According to an aspect of some embodiments of the present invention there is provided a method for determining the presence of an analyte in a sample. In some embodiments, there is provided a method for determining the presence of an analyte in a sample comprising contacting a sample with a device comprising at least a section 1, a section 2, a section 3 and a section 4 arranged in an axial and consecutive order and partially overlapping, wherein section 3 is functionalized with the analyte; and detecting the presence of a signal, thereby determining the presence of the analyte in a sample.

The term "contacting", as used herein, refers generally to providing access of one component, reagent, analyte or sample to another. For example, contacting can involve mixing the device of the invention with a sample comprising the analyte molecule.

In some embodiments, section 1 comprises a sample collecting surface, section 2 comprises a surface functionalized with a recognition molecule having specific affinity to the analyte linked to a reporter molecule, wherein the reporter molecule generates a chemically and/or electrically and/or a physically detectable reaction; and section 4 comprises a surface deposited with a substrate molecule. In some embodiments, section 3 further comprises a calibration area comprising a substrate molecule placed adjacent to section 2. In some embodiments, section 5 comprises an empty surface.

In some embodiments, a sample is placed in section 1, and flows from section 1 to section 2, from section 2 to section 3 and from section 3 to section 4. In some embodiments, a sample is placed in section 1, and flows from section 1 to section 2, from section 2 to section 3, from section 3 to section 4 and from section 4 to section 5.

In some embodiments, detecting the presence of a signal is in calibration area of section 3. In some embodiments, detecting the presence of a signal is in calibration area of section 3 and section 4. In some embodiments, if an analyte is present in a sample, a signal will be detected in calibration area of section 3 and section 4. In some embodiments, if no analyte is present in a sample, a signal will be detected only in calibration area of section 3.

Specifications of section 1, section 2, section 3, section 4, and section 5 and detection of a signal are described elsewhere herein.

In some embodiments, the sample diffuses from section 1 to section 5. In some embodiments, all dissolved or dispersed components of the sample diffuse at substantially equal rates and with relatively unimpaired flow laterally from section 1 to section 5.

In some embodiments, there is provided a method for quantifying the amount of an analyte in a sample, further comprising quantifying the amount of the signal in calibration area and correlating the signal intensity data from calibration area with signal intensity data from section 4.

In some embodiments, there is provided a method for diagnosing an infectious disease.

In some embodiments, there is provided a method for diagnosing a pathogen or a subcomponent thereof for which known biomarkers exist as well as existing special affinity bioreceptors such as antibodies.

In some embodiments, the presence of a signal can be detected after 1 min to 40 min of applying a sample in section 1. In some embodiments, the presence of a signal can be detected after 1 min to 30 min, 1 min to 20 min, 1 min to 15 min, 1 min to 10 min, 2 min to 30 min, 5 min to 30 min, 5 min to 20 min, 5 min to 15 min, or 5 min to 10 min, of applying a sample in section 1, including any range therebetween.

According to some embodiments of the present invention, there is provided a method which utilizes specific binding members.

The Kit

According to an aspect of some embodiments of the present invention there is provided a kit, comprising: a section 1 comprising a sample collecting surface; a section 2, comprising a surface deposited with a recognition molecule having specific affinity to an analyte linked to a reporter molecule, wherein a reporter molecule generates a chemically and/or electrically and/or a physically detectable reaction; a section 3 functionalized with an analyte and comprising a calibration area comprising a substrate molecule; and a section 4 comprising a surface deposited with a substrate molecule; a section 5 comprising surface to contain excess material.

In some embodiments, a kit according to the present invention comprises instructions for connecting a section 1, a section 2, a section 3, a section 4 and a section 5 in an axial and consecutive order and partially overlapping.

In some embodiments, the kit further comprises a sample collecting instrument. In some embodiments, a sample collecting instrument is a graduated measuring instrument. In some embodiments, a sample collecting instruments is used to collect a sample applying the sample in the sample collecting surface. Non-limiting examples of collecting instruments that can be used according to the present invention include swab, wooden spatula, pipette or other form of sample collecting apparatus.

In some embodiments, the kit comprises at least two sections 4 each one of them comprising different substrate molecules. In some embodiments, at least one of the substrates comprises an active-pixel sensor (APS) or an electrode.

According to some embodiments of the invention, there is provided kit for determining the presence of an analyte in a sample.

In some embodiments, there is provided a kit for diagnosing an infectious disease.

General

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Reagents

Phosphate-buffered saline (PBS) tablets (cat. no. P4417), 3-(Glycidoxypropyl)trimethoxysilane (GPTMS)(440167, 98% (v/v)) and sodium m-periodate (S1878) were purchased from Sigma-Aldrich. PBS-0.05% (v/v) Tween (PBST) was prepared by adding 0.5 mL of Tween-20 solution (cat. no. P7949) to 1 L of PBS buffer. The 5% (w/v) skim milk (SM) solution was prepared by adding 5 g of SM powder (70166) to 100 mL of PBS solution. Milli-Q ultrafiltered (UF) H2O (with a resistivity of 18.2 MΩ/cm at 25° C.) was used in preparation of all solutions, luminol-$H_2O_2$ substrate solution (ratio 1:1) (cat. no. 1705040, BioRad), Methyl alcohol (136805) was purchased by Bio-Lab (Israel), acetic acid (45731, 99.8% (v/v)) was purchased from Fluka, hydrochloric acid (7647010, 37% (v/v)) and hydrogen peroxide solution (7722841, 35% (v/v)) were purchased from Acros Organic (USA).

Immunoreagents

Dengue NS1 protein (His tag) (Fitzgerald, Cat. no. 80-1348), was purchased from Tarom, Israel, Mouse monoclonal anti-Dengue Virus, NS1 antibody (IgG), with conjugated HRP enzyme (USBiological, Cat. no. 143056-HRP), was purchased from Biotest, Israel.

Device Fabrication

Membranes. Conjugate release matrix (cat. no. PT-R5), and absorbent (cat. no. AP-080) pads were purchased from Advanced Microdevices Pvt. Ltd. (India).

Assay Reagent Immobilization Procedures

Substrate pads were made by cutting 40×5 mm pads from absorption pads, wetting with 300 µL of luminol-$H_2O_2$ substrate solution (ratio 1:1) (cat. no. 1705040, BioRad), and drying for 2 h at 37° C. in the dark. Conjugation pads (10×3 mm) were prepared by wetting pads with 35 µL of anti-Dengue NS1 antibodies-HRP conjugated (diluted with PBS (0.203 g L−1 $NaH_2PO_4$, 1.149 g L−1 $Na_2HPO_4$, 8.5 g L−1 NaCl) (pH 7.2)) and dried for 20 min at 37° C. Sample pads were made cutting 10×5 mm of empty Conjugation pads. The conjugate pads were stored at 100% humidity at room temperature until used. Blocking layer was prepared similar to the reference protocol described by Liebes et al. and Algaar et al. Briefly, Conjugate release matrix (cat. no. PT-R5) were exposed to methanol/97% HCl solution for 20 min, cleaned by sonication in DDW for 20 min and treated with 7:3 [v/v] 97% $HCl/H_2O_2$ solution for 10 minutes at 90° C. to produce surface hydroxyl groups, rinsed with nanopure water and dried with nitrogen gas. The membrane surfaces were then silanized with (3-glycidoxypropyl)trimethoxysilane for 60 min at 60° C. Then, treated with 11.6 mM hydrochloric acid for 60 min at 50° C. (formation of vicinal diols) and 100 mM sodium m-periodate dissolved in 10% (v/v) acetic acid for 60 min at room temperature without exposure to light (oxidation to aldehyde). Membranes were then rinsed with deionized water and incubated with 10 mL of 200 ng mL$^{-1}$ NS1 overnight at 4° C. The next day the membranes were washed 3 times using PBST for 5 min each time and dried for 40 min at RT° C.

Measurement Procedure

360 µL aqueous sample was applied on top of the sample pad. The sample passes through the membranes and exert specific interactions. Target analytes first diffuse within the membrane with the labeled anti-NS1 antibodies, then move on through the blocking layer to the absorption pad containing the dried substrate molecule so as the reaching enzymes react to generate signal. In samples containing the target protein, the light signal produced was captured with a CCD camera (Retiga-SRV FAST 1394, InterFocus, U.K.). The CCD camera was placed 30 cm above the strip, and serial pictures of 1.5 mins of exposure time were taken with QCapture pro software. Measurement occurred 5 min after the strip was exposed to the liquid sample.

Optimization Steps

Determining Blocking Potential with Increasing Immobilized NS1 Concentrations

To assess potential blocking ability with use of higher protein concentration to prevent false positive response in detection. 5×15 mm conjugate pads were treated according to protocol described previously and incubated overnight with increasingly higher concentrations of NS1 (0, 100, 500, 1000, 1500, 2000 ng mL$^{-1}$). After, the pads were washed 3 times in PBST, incubated with anti-NS1 antibodies-HRP attached 1/15,000 dilution in PBS for 1 hour in RT, then washed again 3 times in PBST. 100 µL Luminol:$H_2O_2$ was added to each strip (size 0.5×1.5 cm), then light image was taken using CCD camera.

Determining the Antibodies-HRP Concentration

Antibody-HRP concentration is directly related to the credibility of the platform. If concentration is too high, the blocker layer might overflow and false positive will occur. When concentration is too low the signal will diminish and there is a loss in sensitivity in detection. The setup was prepared as mentioned in Assay Reagents Immobilization Procedure section, only with different dilution of anti-NS1-HRP (1/5 k, 1/7.5 k, 1/10 k, 1.25 k) in PBST 0.05% v/v.

Sensitivity Test in an Optimized Membrane Setup

After optimization, the membrane-based setup's sensitivity to Dengue NS1 was tested and compared to sensitivity achieved by ELISA. Both technics were tested against samples of PBS spiked for different concentrations of Dengue NS1 (1, 5, 25, 125, 600, 3000 ng mL$^{-1}$). All immobilization procedures and pad preparation were previously described in the Assay Reagents Immobilization Procedure section. The setup design was explained in the Assembly of the Membrane Based Immunoassay Setup section. 360 µL samples were applied slowly above the sample pad, and after 5 minutes measurements were taken using a CCD camera. Each repetition for all different NS1 concentration was made in a different day anew (n=3). Fit for linear response between signal strength and NS1 concentration in sample was computed between 5 and 600 ng mL$^{-1}$.

Spiked Serum Sample

Porcine serum samples were spiked to achieve concentration of 500 ng mL$^{-1}$ and tested using the Capture flow assay for the presence of Dengue NS1. 40 µL of each sample was diluted with 360 µL PBS, then applied onto the setup. Light reaction was recorded using CCD camera and analyzed in ImageJ.

Data Analysis

For each measurement received using the CCD camera, a TIF format file was created and analyzed with ImageJ software (US National Institutes of Health). A threshold was set for pixel brightness and areas of luminescence were measured for total light intensity.

Example 1

Assembly of the Membrane Based Immunoassay Setup for Detection and Quantification of Denge NS1

A proposed setup is composed of layers made of materials previously used for diagnostic purposes. At the start of the strip a sample pad will collect the tested sample, next, a conjugate release matrix with awaiting anti-NS1-HRP antibody-reporter. Then, a capture layer of functionalized conjugate matrix with covalently bound Dengue NS1 proteins. At the second end, absorbent pad with substrate molecule to generate signal. The scheme of design works so that once the putative sample is applied it meets the first layer to even the flow rate, the NS1 in sample passes to the next functional membrane where a corresponding anti-NS1-HRP conjugates to create a complex of NS1-anti-NS1-HRP, this immuno-complex then traverses to a functionalized filter like capture layer, containing the pre-attached NS1, the immuno-complex formed will pass inert to the current layer and reach the final layer where a substrate molecule awaits to react with the reporter and create a readable light signal. In the case of an NS1 free sample, the anti-NS1-HRP will stay available to connect to the pre-attached NS1 in the filter like capture layer, thus no signal will be generated at the final layer.

The unique novel capture layer gives an opportunity to take the lateral flow assay technology from 2-dimensional platform to a 3-dimensional matrix, allowing for different shapes, the ability to multiplex and quantification in an easy, one step procedure.

The immunoassay was assembled by placing all prepared pads similar to traditional lateral flow immunoassay. The sample, conjugated, capture, and absorbent (substrate molecule) pads were placed one next to the other with roughly 1 mm overlapping in this order on top of a backing card.

Example 2

Optimization and Characterization Steps

The Capture layer is of crucial importance to the technology, capturing unbound antibody-HRP from getting to the absorbent pad prevents unwanted false response. This layer's ability to capture antibodies is dependent on the strength of NS1 binding to the matrix, its availability and amount in the matrix. As described in the Assay Reagent Immobilization Procedure section, the NS1 proteins is covalently bound to the layer's surface with a silane crosslinker doubling as a spacer, the strong covalent bond contributes greatly to prevention of NS1 leaching. The porous shape of the treated conjugate pad allows for high volume of active matrix to contain many NS1 potential capturing molecules.

Figure 7:
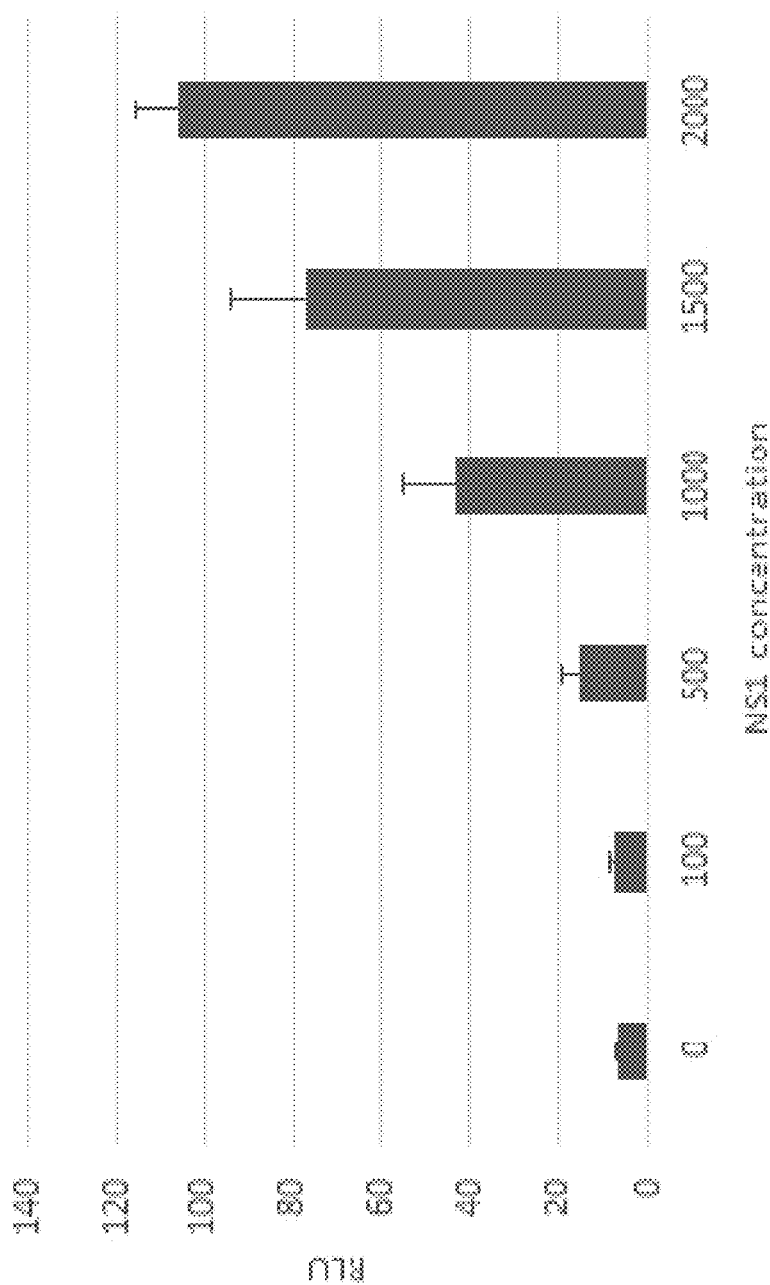
FIG. 7 is a bar graph of the effect of NS1 concentration immobilized on the blocker's capture potential. From left to right, blocker with increasing NS1 concentration in O.N. incubation (0, 100, 500, 1000, 1500, 2000 ng mL$^{-1}$. Respectively), n=4.
Figure 7:
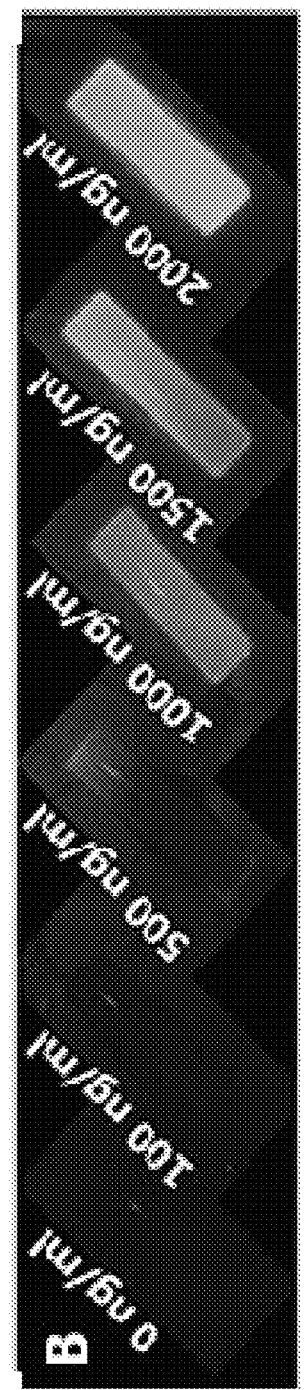

It is shown in FIG. 7 that the amount of capturing agent, in this case Dengue NS1, immobilized on the blocking layer affects the capturing layer potential to filter unbound antibodies. Ideally higher amount of the capturing agent would ensure minimal false positives and maximum capturing ability of antibodies, however, to reduce production cost it is preferable to immobilize the efficient minimum required to prevent false positive responses. In farther experiments a concentration of 200 ng mL$^{-1}$ was used.

The amount of antibodies awaiting the sample determine the potential sensitivity of the setup, optimal antibodies-HRP concentration allows for high amount of conjugations between NS1 in sample and antibodies, thus generate strong light signal while unbound antibodies will not overflow the blocking layer and leak to generate false positive response.

Figure 8A:
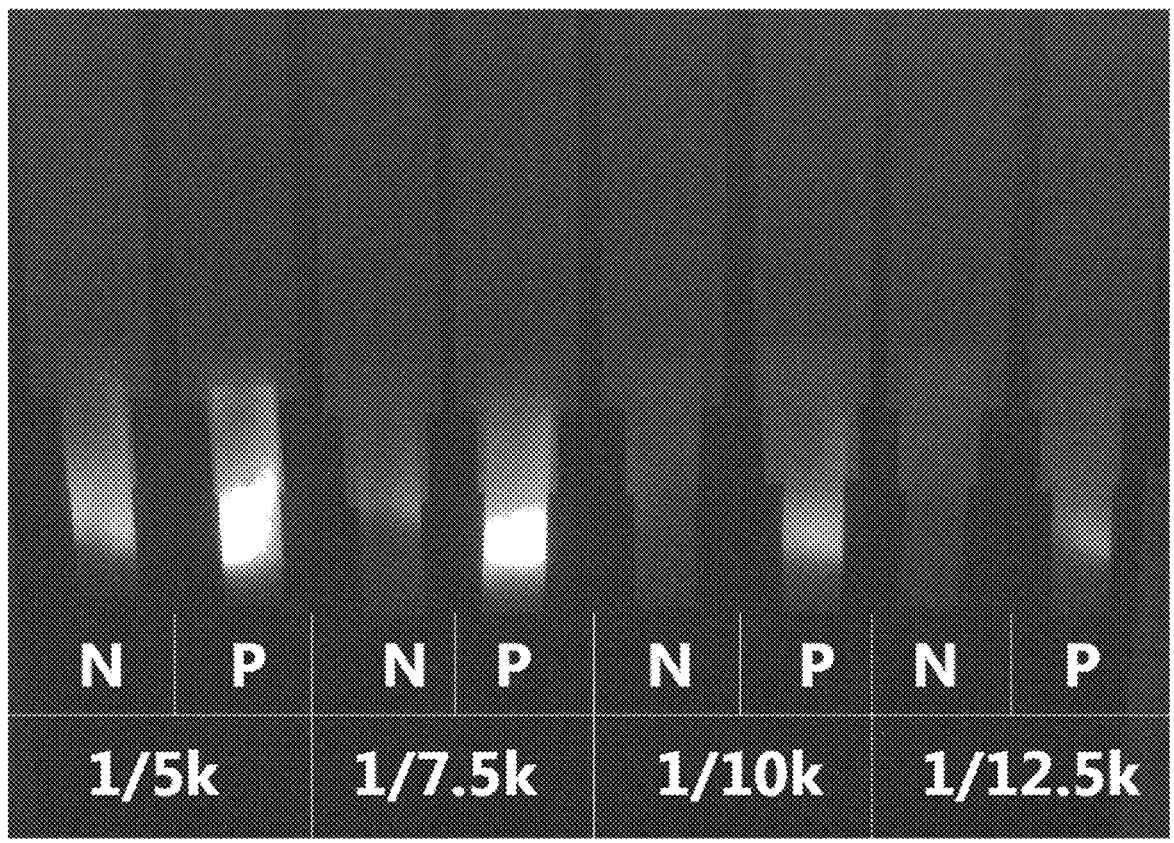
FIGS. 8A-B present the effect of antibodies concentration on signal resolution; photo taken using CCD camera (FIG. 8A) and numerical presentation of signal generated with imageJ, n=3 (FIG. 8B)
Figure 8B:
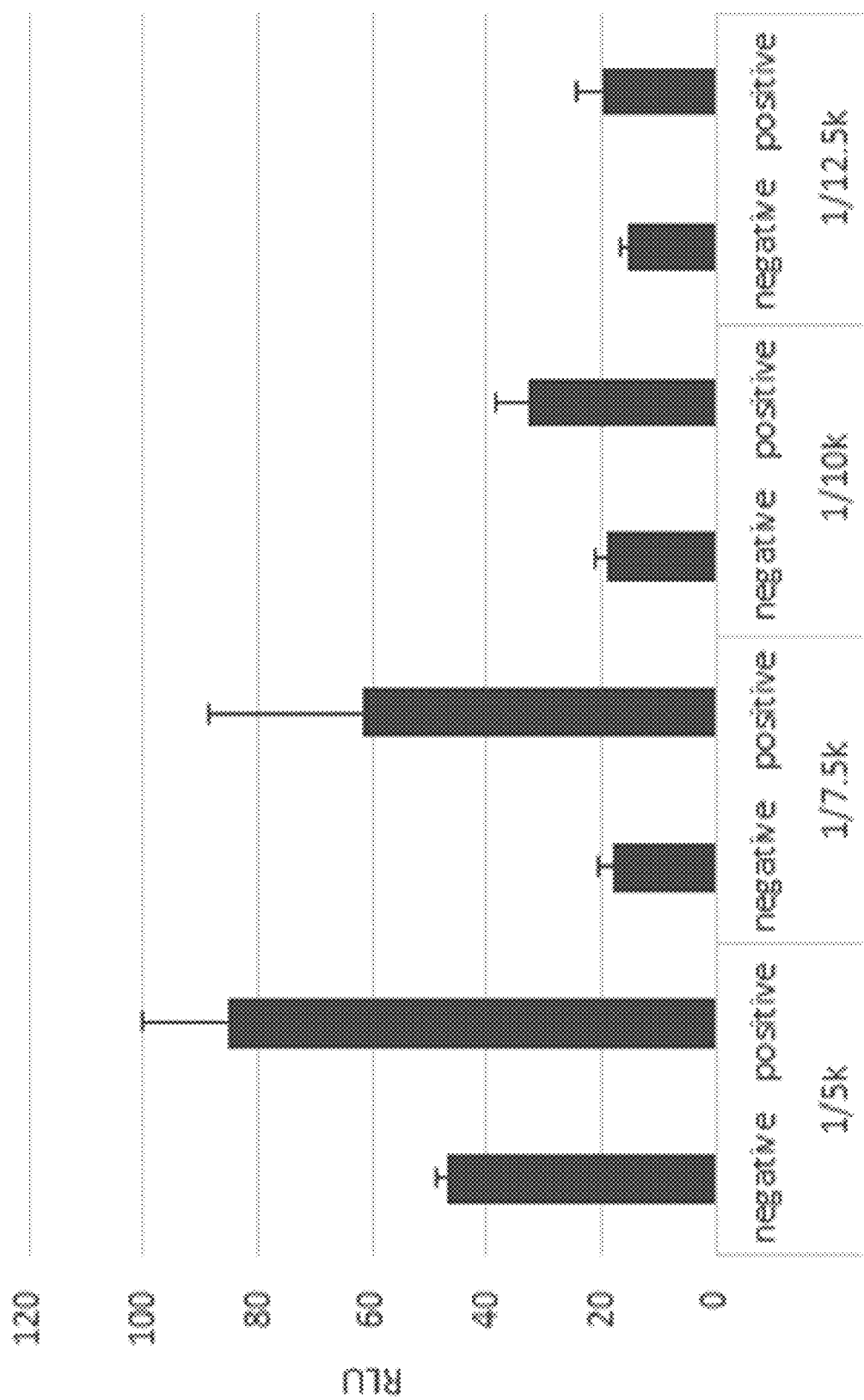

The optimal antibodies dilution was determined (FIGS. 8A-B) at 1/7.5 k, up to dilution of 1/7.5 k there is no major difference in light signal with a negative sample, however in concentration of 1/5 k there is a significance increase in negative signal, this means that unbound antibodies overflowed the blocker and reached the absorbent pad without NS1 protein from the sample. 1/7.5 k generates the strongest true positive response without generating strong false positives, this concentration can give the highest sensitivity in the system.

Example 3

Sensitivity Test in an Optimized Membrane Setup

Assessment of our current setup was made with comparison to ELISA as a benchmark. ELISA is often used for comparison in quantification of proteins.

Figure 9A:
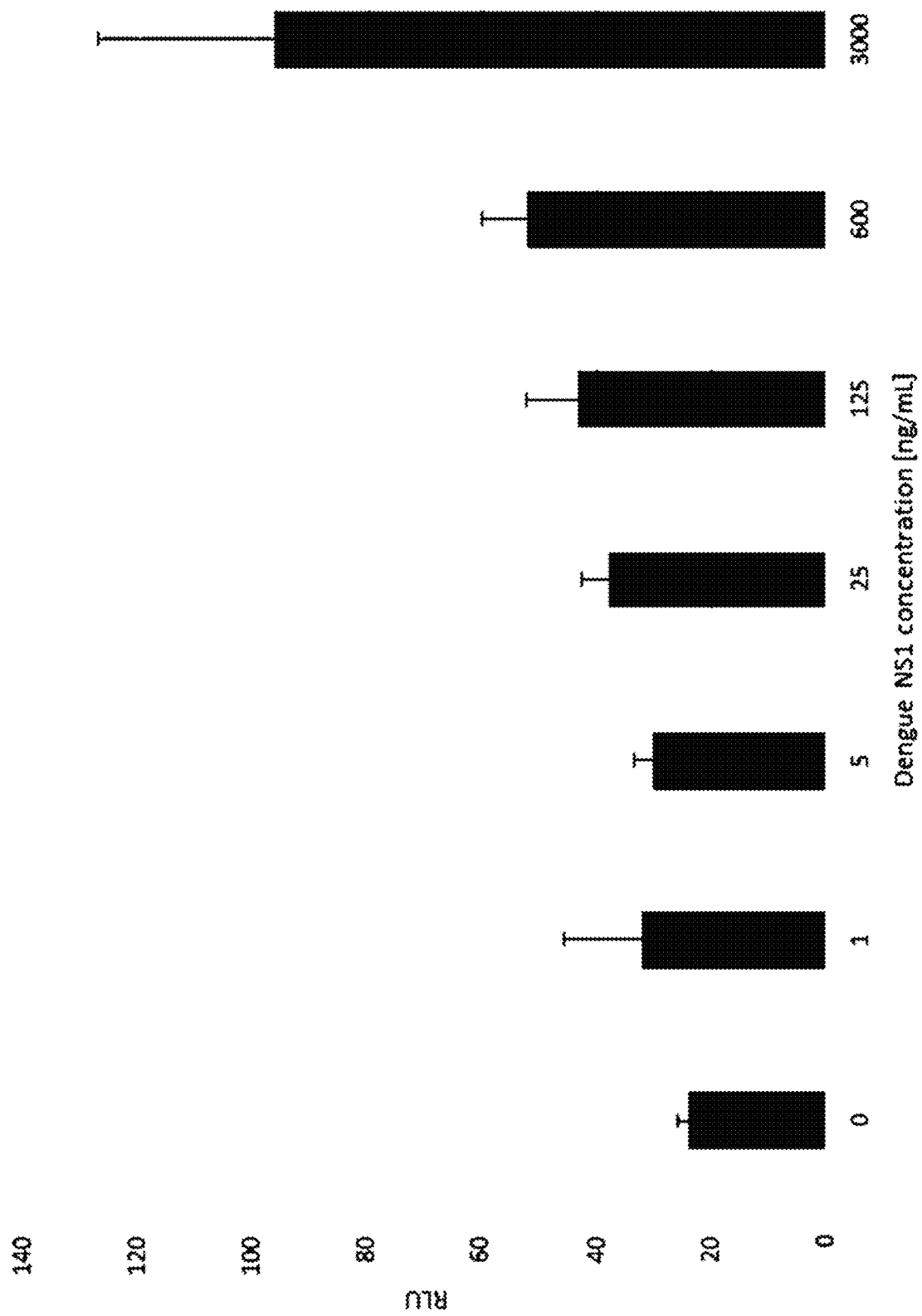
FIGS. 9A-B are bar graphs showing the response of the setup to samples spiked with NS1 (FIG. 9A), and chemiluminescent test with ELISA to different NS1 concentrations (FIG. 9B)
Figure 9B:
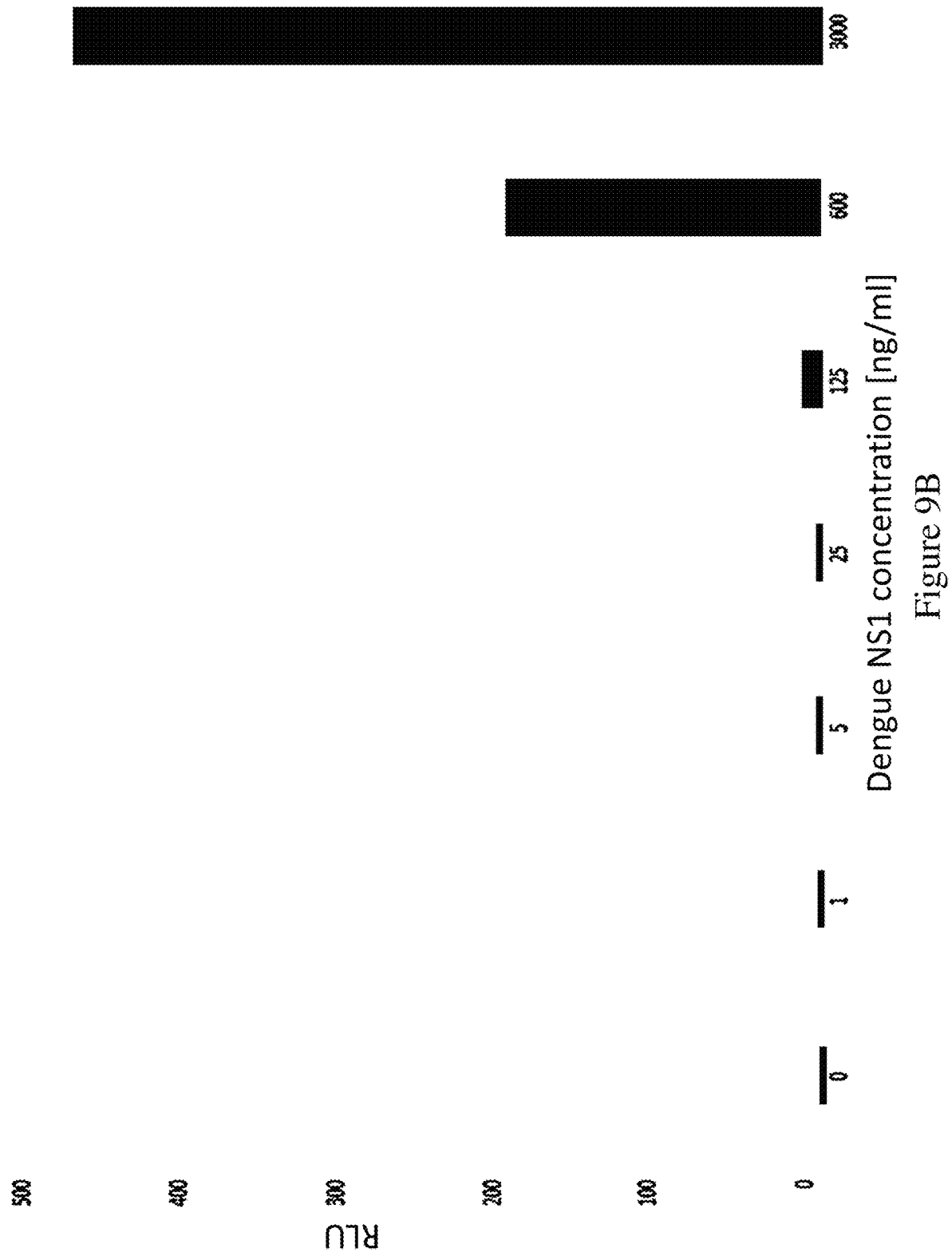

The lowest concentration of NS1 detected with the inventor's setup was 5 ng mL$^{-1}$ (FIG. 9A), it is 5 times lower than the sensitivity limit reached with ELISA (25 ng mL$^{-1}$) (FIG. 9B). A linear fit for response between 5 and 600 ng mL-1 was built with $R^2=0.9921$ (data not shown).

Example 4

Spiked Serum Testing

Current clinical samples that are taken from patients are serum, hence it is essential for setup to be proven to detect the target analyte in a serum sample.

Figure 10A:
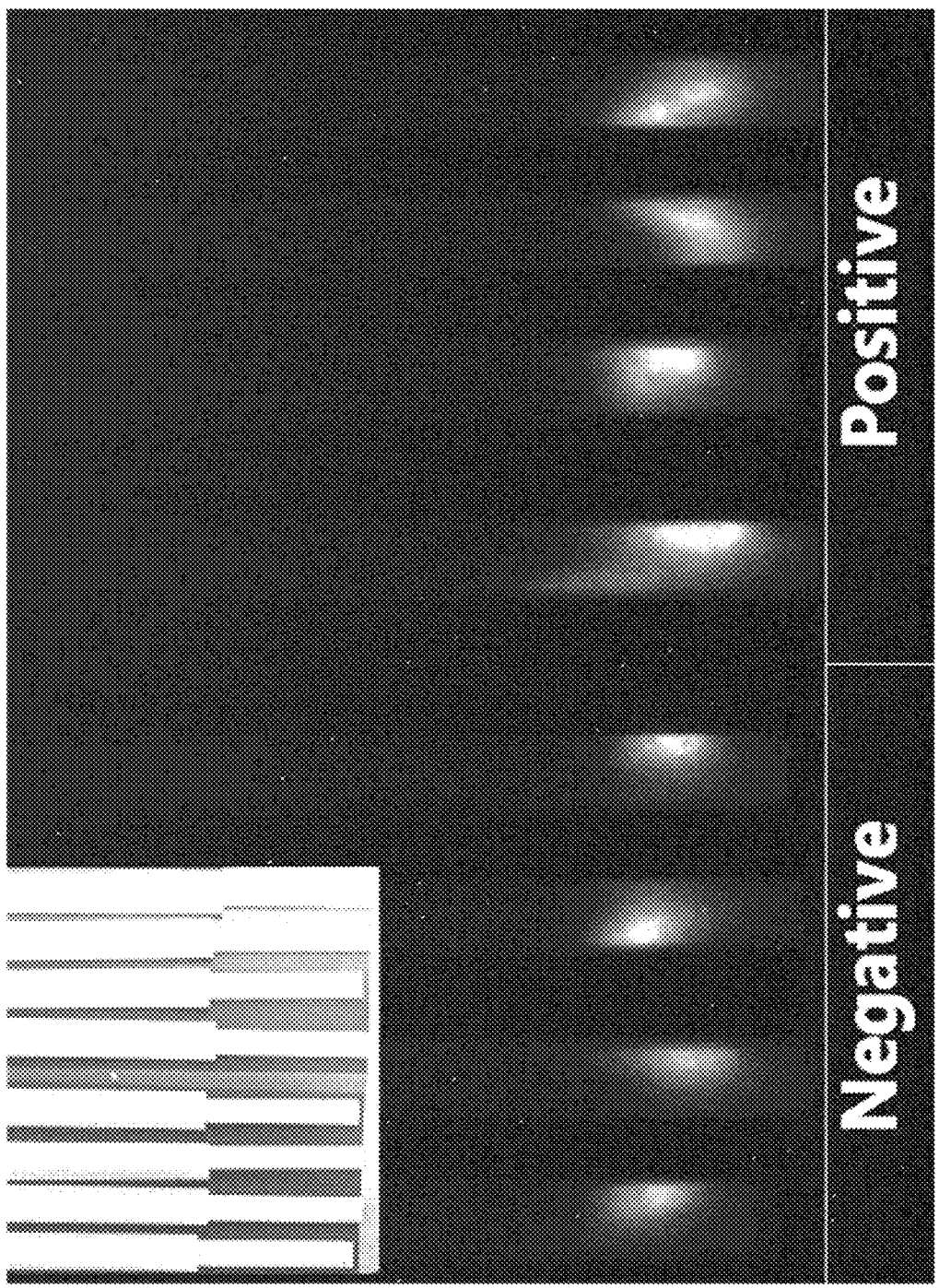
FIGS. 10A-B present the setup response to serum sample spiked with NS1 at 60 ng mL$^{-1}$; picture image taken using a CCD camera (FIG. 10A), and numerical analysis using InageJ software (FIG. 10B).
Figure 10B:
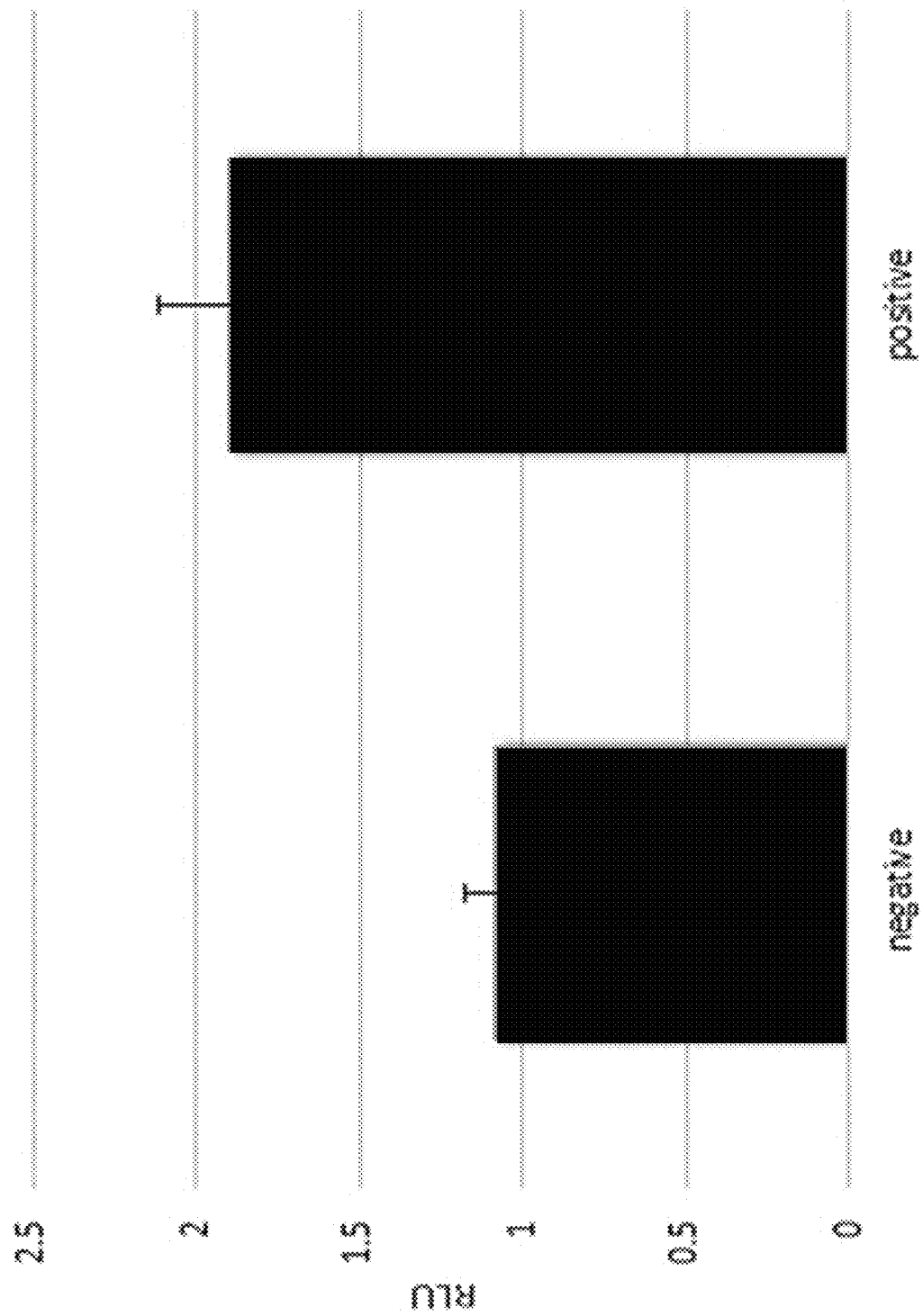

FIGS. 10A-B shows higher light intensity where a positive sample was applied. This proves the ability of the setup to detect NS1 analyte in a serum sample.

Example 5

Calibration Line Effect on Result Certainty

Capture membrane of 10×70 mm polyester was immobilized O.N. with hTg at concentration 2000 ng/mL. Conjugate release pads were prepared by applying 35 uL of anti-hTg diluted in PBST 0.05% with 2% trehalose onto 12×4 mm native polyester membrane and drying at 30° C. for 60 minutes. Absorbent pad was applied with 300 uL of TMB substrate and dried at 40° C. for 2.5 hours in dark. Calibration line of 12×4 mm native polyester membrane was soaked in TMB and dried for 30 minutes at 40° C. Native 4×12 mm polyester membrane was used as a sample pad.

Sample contained 300 uL of 1:50 diluted porcine serum. Positive control contained 1000 ng/ml of hTg. Negative control contained no hTg.

After sample application, an image was taken using a smartphone camera. Picture analysis was made using imageJ software.

Figure 11:
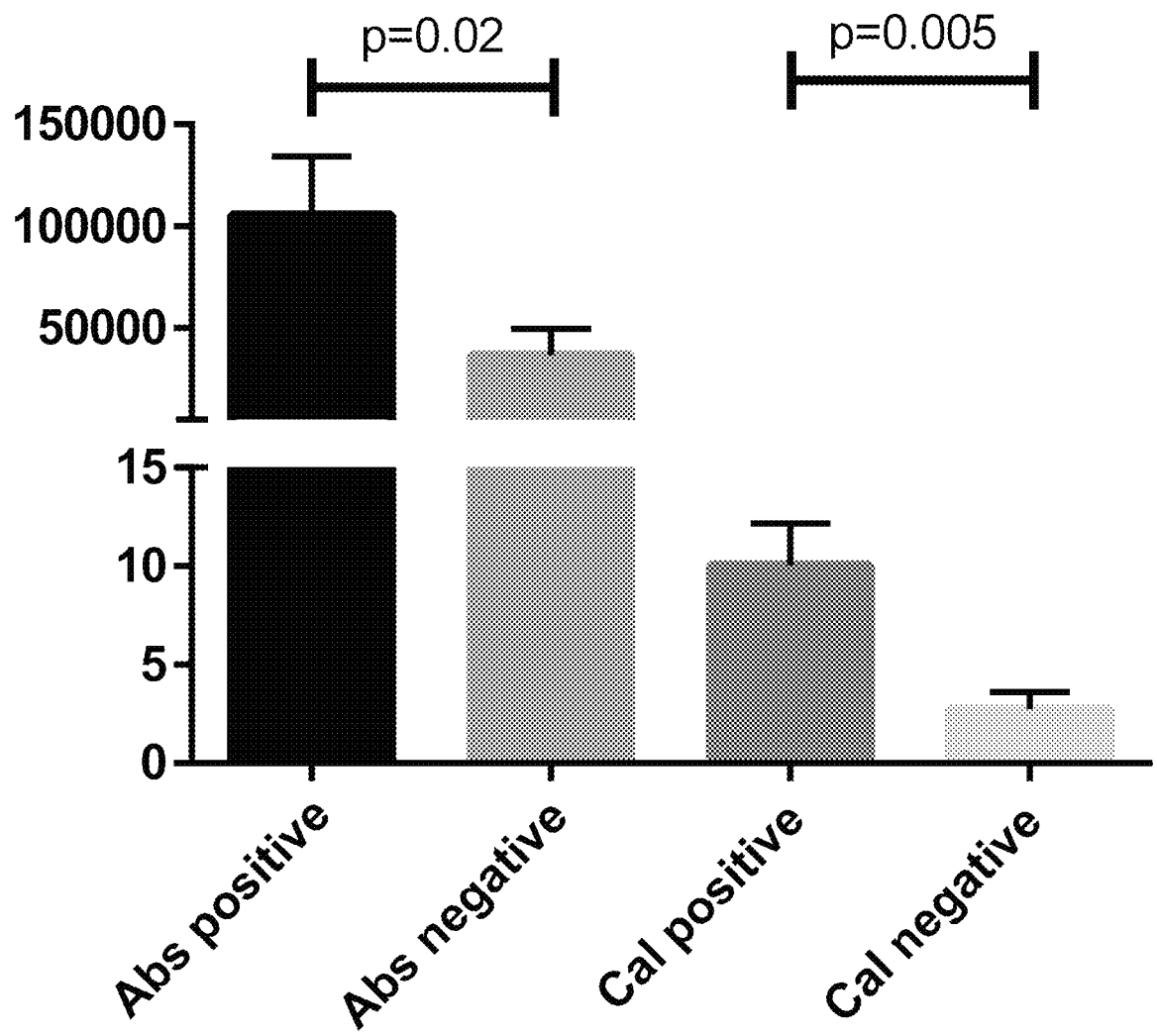
FIG. 11 shows a bar graph representing responses of the device to positive and negative samples. The two left columns represent absolute response values measured at the absorbent pads, the two right columns show normalized values calculated as a ratio of the absolute response value measured at the absorbent pad and the response absolute response value measured at the calibration line.

As represented in FIG. 11, positive response of the platform is higher than negative response. However, the probability value (p-value) for the absolute values was 0.019, while the calculated p-value for the relative values was significantly lower (p-value=0.0054). This result show that by applying the calibration concept, the certainty of the measurement increases.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for detecting an analyte in a sample, the device comprising a section 1, a section 2, a section 3, a section 4, and a calibration area wherein:
   a. said section 2 is coupled to said section 1, said section 2 comprises a surface comprising a recognition molecule having specific affinity to said analyte, wherein said recognition molecule is linked to a reporter molecule, and wherein said reporter molecule generates a trigger whether bound to said analyte or not;
   b. said section 3 is coupled to said section 2 and to said section 4, said section 3 comprises a surface functionalized with said same analyte as present in the sample, wherein binding of said reporter molecule to said analyte in section 3 produces a reduced signal indicating an analyte negative sample; and
   c. sections 1 to 4 are arranged along a horizontal axis and in fluid communication allowing lateral flow of fluid from said section 1 through said section 2 and said section 3 to section 4, and said section 4 comprises a surface in contact with a substrate molecule generating a signal in response to said reporter molecule.

2. The device of claim 1, wherein said section 1 comprises a sample collecting surface.

3. The device of claim 1, further comprising a section 5 coupled to said section 4 and in fluid communication with said section 4.

4. The device of claim 1, wherein any one of: (i) said section 2 is in contact or partially overlapping with said section 1, and wherein said overlapping is in the range of 0.01% to 99% of the total surface of any one of said section 2 and said section 1; and (ii) said section 3 is in contact or partially overlapping with said section 2 and said section 4, and wherein said overlapping is in the range of 0.01% to 99% of the total surface of any one of said section 2, said section 3, and said section 4.

5. The device of claim 1, wherein said trigger comprises at least one of: a reactive compound, electromagnetic radiation, and a charged particle or a combination thereof.

6. The device of claim 1, wherein said section 3 is devoid of said recognition molecule and said reporter molecule, and wherein said reporter molecule is selected from an enzyme, luminescent compound, fluorescent compound, magnetic particle, or an electrochemically active compound.

7. The device of claim 1, wherein the concentration of said recognition molecule in section 2 and said analyte in section 3 is in the range of 0.01 ug/mL to 100 mg/mL.

8. The device of claim 1, wherein said device comprises any one of: at least three sections are disposed along one or more planes; wherein two consecutive sections are disposed along one or more planes; and wherein all of said sections are disposed along the same plane.

9. The device of claim 1, further comprising a detection unit in operable communication with said device, said detection unit is configured to detect said signal, and wherein said detection unit comprises an element selected form the group consisting of an active-pixel sensor (APS), an electrode, an excitation source with active-pixel sensor, or any combination thereof.

10. The device of claim 1, wherein said analyte or equivalent thereof is selected from virus, proteins, biological cells, toxins and pathogens, pharmaceuticals and drugs.

11. The device of claim 1, wherein said sample is selected from water, blood, urine, sweat, saliva, and serum.

12. A method for determining the presence of an analyte in a sample, comprising:
   a. contacting a sample with the device of claim 1;
   b. detecting the presence of a signal in any one of said calibration area, in said section 4, and in both; and
   c. determining the presence of said analyte in the sample based on comparing the detected signal to a predetermined threshold, wherein:
      i. a reduced signal in section 4 compared to the calibration area indicates the absence of the analyte in the sample; and
      ii. an equivalent signal in section 4 compared to the calibration area indicates the presence of the analyte in the sample.

13. The method of claim 12, further comprising:
   (i) quantifying the amount of said signal in said calibration area and in said section 4; and
   (ii) correlating the signal intensity data from said calibration area with the signal intensity data from section 4, wherein the degree of signal reduction in section 4 compared to the calibration area is proportional to the concentration of the analyte in the sample; and
   (iii) generating a quantitative measurement of the analyte concentration based on a predetermined calibration curve relating signal reduction to analyte concentration.

14. A kit for diagnosing an infectious disease in a subject in need thereof, comprising:
   (i) a section 1 comprising a sample collecting surface;
   (ii) a section 2, comprising a surface deposited with a recognition molecule having specific affinity to an analyte linked to a reporter molecule, wherein said reporter molecule generates a chemically and/or an electrically and/or a physically detectable reaction whether bound to said analyte or not;

(iii) a section 3 functionalized with said analyte, wherein binding of said reporter molecule to said analyte in section 3 produces a reduced signal indicating an analyte negative sample;

(iv) a section 4 comprising a surface deposited with a substrate molecule generating a signal in response to said reporter molecule; and (v) a section 5 comprising a surface available for holding excess sample, and wherein the kit-further comprises a calibration area.

15. The kit of claim 14, further comprising instructions for arranging section 1, section 2, calibration area, section 3, section 4 and section 5 along a horizontal axis and in fluid communication allowing lateral flow from section 1 throughout all sections to section 5.

16. The kit of claim 14, further comprising a sample collecting instrument.

17. The kit of claim 14, comprising at least two sections 4 each one of them comprising different substrate molecules.

18. The kit of claim 17, wherein a surface of said at least two sections 4 comprises an active-pixel sensor (APS), an electrode, or an excitation device with an active-pixel sensor (APS).

19. The device of claim 1, wherein said calibration area is: (i) disposed between said section 2 and said section 3; and (ii) comprises a surface in contact with said substrate molecule.

20. The kit of claim 14, wherein said diagnosing said infectious disease in said subject is based on determination of a presence of said analyte in the sample obtained or derived from said subject.

* * * * *